US009081193B2

(12) United States Patent
Gelernt et al.

(10) Patent No.: US 9,081,193 B2
(45) Date of Patent: *Jul. 14, 2015

(54) INTERFEROMETRIC SYSTEMS AND METHODS

(71) Applicant: The Arizona Board of Regents on Behalf of The University of Arizona, Tucson, AZ (US)

(72) Inventors: Barry Gelernt, Oceanside, CA (US); Thomas D. Milster, Tucson, AZ (US); Thiago Jota, Tucson, AZ (US)

(73) Assignees: The Arizona Board of Regents on Behalf of the University of Arizona, Tucson, AZ (US); Invent Technologies LLC, Oceanside, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/924,065

(22) Filed: Jun. 21, 2013

(65) Prior Publication Data
US 2013/0278922 A1 Oct. 24, 2013

Related U.S. Application Data

(63) Continuation-in-part of application No. 12/304,494, filed as application No. PCT/US2007/071003 on Jun. 12, 2007, now Pat. No. 8,472,111.

(60) Provisional application No. 60/812,912, filed on Jun. 13, 2006.

(51) Int. Cl.
*G02B 21/16* (2006.01)
*G01N 21/45* (2006.01)
(Continued)

(52) U.S. Cl.
CPC ............... *G02B 21/16* (2013.01); *G01J 3/0208* (2013.01); *G01J 3/10* (2013.01); *G01J 3/453* (2013.01); *G01N 21/45* (2013.01); *G01N 2021/451* (2013.01)

(58) Field of Classification Search
CPC ................... G02B 21/16; G01N 2021/451
USPC .......................................... 359/350; 356/496
See application file for complete search history.

(56) References Cited

U.S. PATENT DOCUMENTS 3,507,987 A 4/1970 Bosch
4,617,531 A 10/1986 Bowlds et al.
(Continued)

FOREIGN PATENT DOCUMENTS

CN 1987660 A 6/2007
CN 101351746 B 11/2011
(Continued)

OTHER PUBLICATIONS

S. Y. Park et al. "A redetermination of the argon content of air for buoyancy corrections in mass standard comparisons", Oct. 2004, Institute of Physics Publishing (IOP), Metrologia, 41, pp. 387-395.*
(Continued)

*Primary Examiner* — Thomas K Pham
*Assistant Examiner* — Marin Pichler
(74) *Attorney, Agent, or Firm* — Whyte Hirschboeck Dudek S.C.

(57) ABSTRACT

Optical systems and methods including interferometric systems and methods are disclosed herein. In some embodiments, the present invention relates to a system comprising at least one light source including a deep ultraviolet light source, a lens device, a beam splitter, and a camera device. The lens device receives first light, directs at least some of that light toward a target location, receives reflected light therefrom, and directs at least some of the reflected light toward a further location, where at least part of a light path between the deep ultraviolet light source and the target location is other than a high vacuum. The camera device is positioned at either the further location or an additional location, whereby an image is generated by the camera device based upon at least a portion of the reflected light. Also encompassed herein are interferometric lithography and optical microscopy systems.

19 Claims, 15 Drawing Sheets

(51) Int. Cl.
*G01J 3/10* (2006.01)
*G01J 3/453* (2006.01)
*G01J 3/02* (2006.01)

(56) References Cited

U.S. PATENT DOCUMENTS

| | | | |
|---|---|---|---|
| 4,863,253 | A | 9/1989 | Shafer et al. |
| 5,198,870 | A * | 3/1993 | Kronberg ............... 356/311 |
| 5,331,456 | A | 7/1994 | Horikawa |
| 5,499,282 | A | 3/1996 | Silfvast |
| 6,195,410 | B1 * | 2/2001 | Cash, Jr. .................. 378/43 |
| 6,324,150 | B1 | 11/2001 | Ju |
| 6,343,089 | B1 | 1/2002 | Manos et al. |
| 6,369,398 | B1 | 4/2002 | Gelernt |
| 6,605,815 | B2 | 8/2003 | Gelernt |
| 6,650,357 | B1 | 11/2003 | Richardson |
| 6,801,358 | B2 | 10/2004 | Shafer et al. |
| 7,126,131 | B2 | 10/2006 | Harrison |
| 7,218,592 | B2 | 5/2007 | Park et al. |
| 7,218,596 | B2 | 5/2007 | Gelernt |
| 7,327,444 | B2 | 2/2008 | Naka et al. |
| 7,359,044 | B2 | 4/2008 | Nishiyama et al. |
| 7,394,551 | B2 | 7/2008 | Harrison |
| 7,440,078 | B2 | 10/2008 | Bleeker et al. |
| 7,474,385 | B2 | 1/2009 | Markoya et al. |
| 7,492,442 | B2 | 2/2009 | Markoya et al. |
| 7,561,252 | B2 | 7/2009 | Sewell et al. |
| 7,684,014 | B2 | 3/2010 | Sewell et al. |
| 7,916,291 | B2 | 3/2011 | Milster et al. |
| 8,198,582 | B2 | 6/2012 | Raptakis et al. |
| 8,264,667 | B2 | 9/2012 | Troost et al. |
| 2002/0125445 | A1 * | 9/2002 | Gelernt ................. 250/492.1 |
| 2002/0136144 | A1 * | 9/2002 | Hatano ................. 369/112.23 |
| 2002/0171367 | A1 * | 11/2002 | Giapis et al. ............ 315/111.21 |
| 2002/0176590 | A1 * | 11/2002 | Ohsaki et al. .............. 356/512 |
| 2002/0191195 | A1 * | 12/2002 | Ichihara et al. ............. 356/521 |
| 2003/0043472 | A1 | 3/2003 | Mandella |
| 2004/0022888 | A1 * | 2/2004 | Sreenivasan et al. ....... 425/174.4 |
| 2004/0228158 | A1 * | 11/2004 | Gelernt .................. 365/106 |
| 2005/0111081 | A1 | 5/2005 | Shafer et al. |
| 2005/0254049 | A1 | 11/2005 | Zhao et al. |
| 2006/0012780 | A1 | 1/2006 | Nishiyama et al. |
| 2006/0044539 | A1 | 3/2006 | Markoya et al. |
| 2006/0050146 | A1 | 3/2006 | Richardson |
| 2006/0072419 | A1 | 4/2006 | Tukker et al. |
| 2006/0170896 | A1 | 8/2006 | Markoya et al. |
| 2007/0070321 | A1 | 3/2007 | Markoya et al. |
| 2007/0139633 | A1 | 6/2007 | Bleeker et al. |
| 2007/0153250 | A1 | 7/2007 | Sewell et al. |
| 2007/0258078 | A1 | 11/2007 | Troost et al. |
| 2008/0129973 | A1 | 6/2008 | McCafferty et al. |
| 2008/0186579 | A1 | 8/2008 | Solak |
| 2008/0204711 | A1 * | 8/2008 | Harrison et al. ................ 356/51 |
| 2008/0304522 | A1 | 12/2008 | Mills |
| 2009/0168152 | A1 * | 7/2009 | Gelernt et al. ................ 359/353 |
| 2009/0236543 | A1 | 9/2009 | Ooki et al. |
| 2010/0053599 | A1 | 3/2010 | Milster et al. |

FOREIGN PATENT DOCUMENTS

| | | |
|---|---|---|
| EP | 1656587 A2 | 5/2006 |
| EP | 1810085 A2 | 7/2007 |
| EP | 1810085 B1 | 7/2007 |
| EP | 1801655 A3 | 8/2007 |
| EP | 1630615 A3 | 1/2008 |
| EP | 1881372 A3 | 2/2008 |
| EP | 1966651 A2 | 9/2008 |
| GB | 1495104 | 12/1977 |
| WO | 2005013194 A2 | 2/2005 |
| WO | 2006045439 A3 | 5/2006 |
| WO | 2007078515 A3 | 7/2007 |
| WO | 2007146938 A2 | 12/2007 |

OTHER PUBLICATIONS

Arioukov et al., "Schwartzschild Objective for Soft X-rays," (Opt. Eng. 39 (8), (2000); pp. 2163-2170.

Atwood et al., "X-ray microimaging for the life sciences," EDB 90: 159921, NDN-108-0533-3189-9, Conference date: (May 24-May 26, 1989); 9 pages.

Chen et al., "Near-Field Solid Immersion Lens (SIL) Microscope with Advanced Compact Mechanical Design," Proc. SPIE, vol. 5380, (Sep. 2004); pp. 634-664.

Chen et al., "Experimental investigation of solid immersion lens lithography," Proc. SPIE, vol. 5754, (May 2005); pp. 254-261.

David et al., "Ultraviolet reflectance of AlN, diamond-like carbon, and SiC thin films," Appl. Phys. Lett., 57 (11); (1990); pp. 1093-1095.

De Wolf, "Raman Spectroscopy: About Chips and Stress," Spectroscopy Europe, 15/2, (2003); pp. 6-13.

Y. Fan, A. Bourov, L. Zavyalova, J. Zhou, A. Estroff, N. Lafferty, B.W. Smith, "ILSim—A compact simulation tool for interferometric lithography," Proc. SPIE 5754 (2005).

Gelernt et al., "Quenching and Radiative Lifetimes for NH (b1ϵ+, v1=0)," Chem. Phys. Lett. 36, 238 (1975).

Grey, "A new series of microscope objectives: I. Catadioptric Newtonian Systems," J. Opt. Soc. Am., 39, 719 (1949).

Grey, "A new series of microscope objectives: II. Preliminary Investigation of catadioptric Schwarzschwarzschild systems," 39, 723 (1949).

Grey, "New series of microscope objectives: III. Ultraviolet objectives of intermediate numerical aperture," 40, 283 (1950).

Hamamatsu, Data Sheet for BT(Back-thinned)-CCD Digital Camera C8000-10, Hamamatsu Photonics, K.K. of Hamamatsu City, Japan, (Jul. 2001) 2 pages.

Jobin-Yvon Raman Applications, No. 01, available at http://www.jobinyvon.com/Raman/Semiconductor_Applications.

Joshi, "Generation of Radiation by Intense Plasma and Electromagnetic Undulators," Final Technical Report, Submitted by: The Regents of the University of California University of California, Los Angeles School of Engineering and Applied Science Los Angeles; (Oct. 1991); 80 pages.

Si Khonina and H. Golub, "How low can STED go? Comparison of different write-erase beam combinations for stimulated emission depletion microscopy," J. Opt. Soc. Am. A, 29(10), (2012) p. 2242.

Khulbe, et al., "Raman scattering from oval defects in GaAs epilayers," Applied Physics Letters, vol. 63, Issue 4, (Jul. 1993); pp. 488-490.

Korsch, "Reflective Optics," Aademic Press, San Diego, (1991); 4 pages.

Liberman et al., "Prospects for photolithography at 121 nm," J. Vac. Sci. Technol. B, vol. 20, No. 6, (Nov./Dec. 2002); pp. 2567-2573.

T. J. MacArthy, D. E. Murnick, M. Salvermoser and A. Ulrich, "Non-thermal Doppler-broadened Lyman-alpha line shape in resonant dissociation of H2," J. Phys B, At. Opt Phys. 38, (2005) p. 3043.

MacDonald, "Microwave Breakdown in Gases," John Wiley, New York, (1966).

T.D. Milster, J.S. Jo, K. Hirota, "Roles of propagating and evanescent waves in solid immersion lens system," Appl. Opt., vol. 38, No. 23, (1999) 5046.

Milster et al., "Maskless Lithograph with Solid Immersion Lens Nano Probes," Proc. SPIE, vol. 5567, (Dec. 2004); pp. 545-556.

Miyata, "Reflecting microscope objectives with nonspherical mirrors," J. Opt. Soc. Am., 42, 431 (1952).

Norris et al., "Reflecting microscopes with spherical mirrors," J. Opt. Soc. Am., 41, 111; (1951).

Novotny, et al., "Principals of Nano-optics", Nanoscale optical microscopy, (2006); 14 pages.

Office Communication; European Patent Application No. 07798444. 1; (Oct. 6, 2011); 9 pages.

E. Palik, Handbook of Optical Constants of Solids; excerpts concerning refractive indices of chromium, copper, magnesium fluoride, amorphous silicon, silicon dioxide, silicon nitride, and silicon; Academic Press; 1997; pp. 383, 284, 911, 577, 758, 774, 560.

PCT Notification of Transmittal of the International Search Report and the Written Opinion of the International Searching Authority, or the Declaration, relating to International Application No. PCT/US07/71003; date of mailing, (Feb. 20, 2008); 8 pages.

(56) References Cited

OTHER PUBLICATIONS

A. D. Rakić, "Algorithm for the determination of intrinsic optical constants of metal films: application to aluminum," Appl. Opt., vol. 34, (Aug. 1995) pp. 4755-4767.

V. Rastogi, Modem Biology, Pitambar Publishing, 1997; p. III-24.

Response to Office Communication; European Patent Application No. 07798444.1; (Apr. 14, 2010); 19 pages.

Semiconductor Industry Association, "International Technology Roadmap for Semiconductors (ITRS)." http://www.itrs.net (2011).

B.W. Smith, A. Bourov, Y. Fan, L. Zavyalova, N. Lafferty, F. Cropanese, "Approaching the numerical aperture of water—Immersion lithography at 193nm," Proc. SPIE 5377 (2004).

B. Smith, Y. Fan, M. Slocum, L. Zavyalova, "25 nm immersion lithography at 193 nm wavelength," Proc. SPIE 5754 (2005).

Supplementary European Search Report, relating to Application No. EP 07 79 8444; date of completion of search Jun. 16, 2009; 9 pages.

U.S. Appl. No. 12/614,281; United States Patent & Trademark Office; Non-Final Rejection; (Mar. 16, 2010); 11 pages.

U.S. Appl. No. 12/614,281; United States Patent & Trademark Office; Response to Non-Final Rejection; (Jul. 16, 2010); 15 pages.

U.S. Appl. No. 12/614,281; United States Patent & Trademark Office; Notice of Allowance; (Aug. 23, 2010); 18 pages.

U.S. Appl. No. 12/614,281; United States Patent & Trademark Office; Notice of Allowance; (Nov. 15, 2010); 23 pages.

UV Solutions, "High Brightness VUV Lamp" Spec. Sheet, (© 2009) UV Solutions, Inc.; 1 page.

Watanabe, "Ultraviolet Absorption Processes in Upper Atmosphere," Advan. Geophys. 5, 153, (1958); 2 pages.

K. R. Wilson, D. S. Peterka, M. Jimenez-Cruz, S. R. Leone and M. Ahmed, "VUV photoelectron imaging of biological nanoparticles: Ionization energy determination of nanophase glycine and phenylalanine-glycine," Phys. Chem. Chem. Phys. 8, (2006); pp. 1880-1890.

Yoshikawa et al., "Development of an extreme ultraviolet imaging spectrometer for the BepiColombo mission," Advances in Space Research, 33, (2004); pp. 2195-2199.

A. N. Zaidel and Y. A. Schreider, "Vacuum Ultraviolet Spectroscopy," Ann Arbor—Humphrey Science Publishers (1970) pp. 2-20, 47-53 and 280-281.

J. Zhou, Y. Fan, A. Bourov, L. Zavyalova, A. Estroff, N. Lafferty, B. Smith, "Immersion Lithograph Fluids for high NA 193 nm lithography," Proc. SPIE 5754 (2005).

* cited by examiner

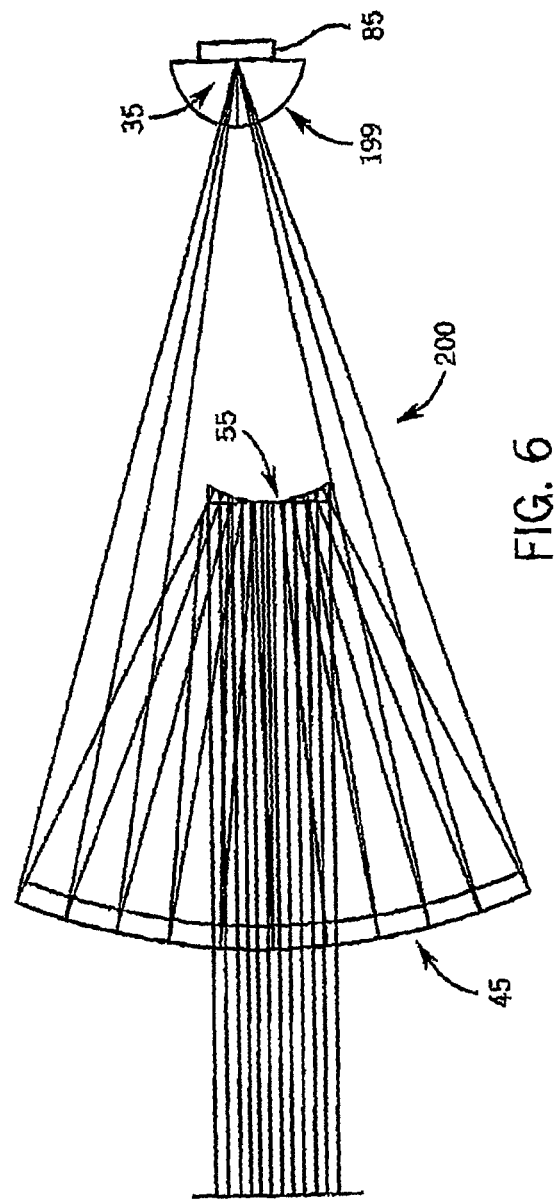

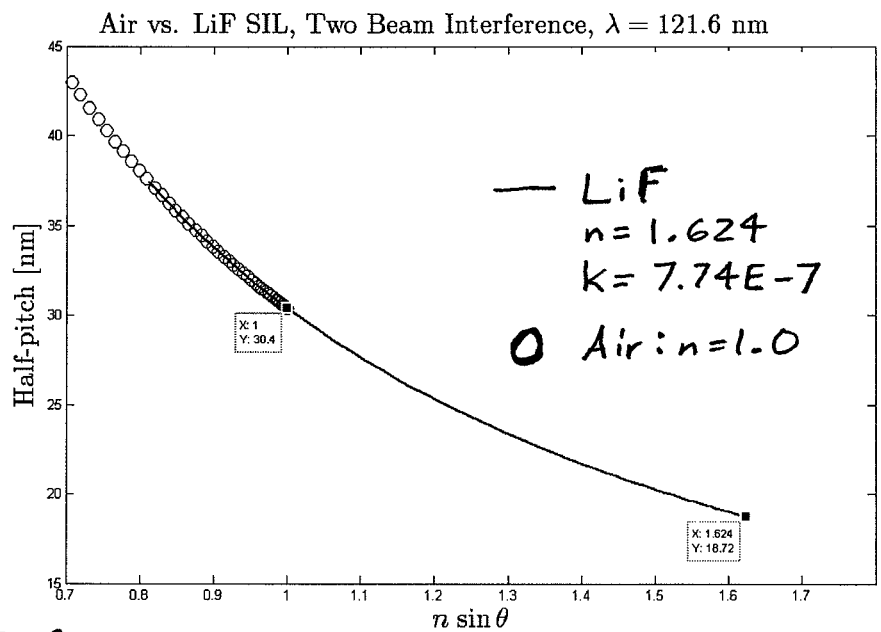
FIG. 19A  CD prediction as a function of NA, where $\theta = \alpha / 2$.
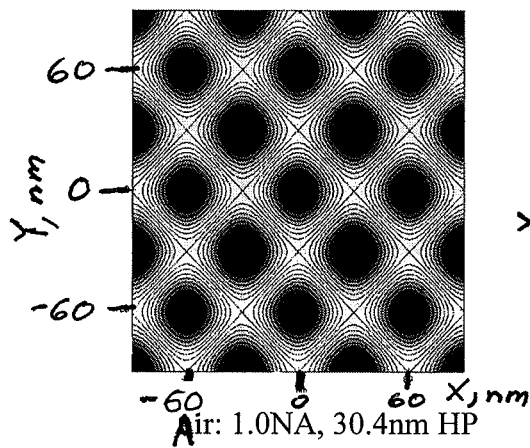
Air: 1.0NA, 30.4nm HP
FIG. 19B
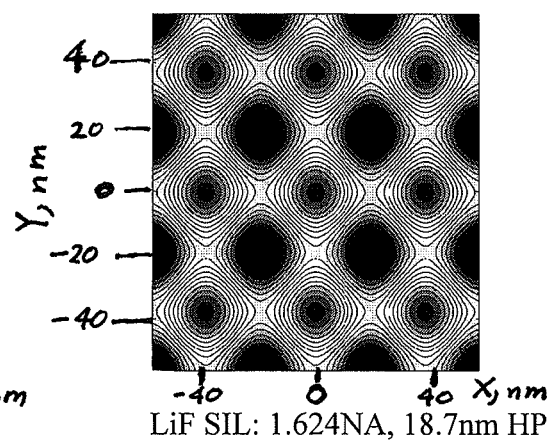
LiF SIL: 1.624NA, 18.7nm HP
FIG. 19C

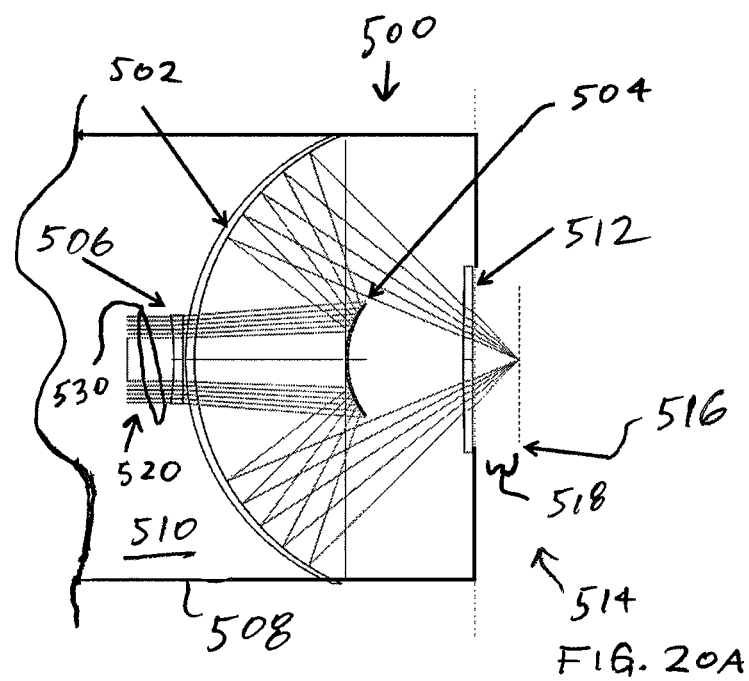
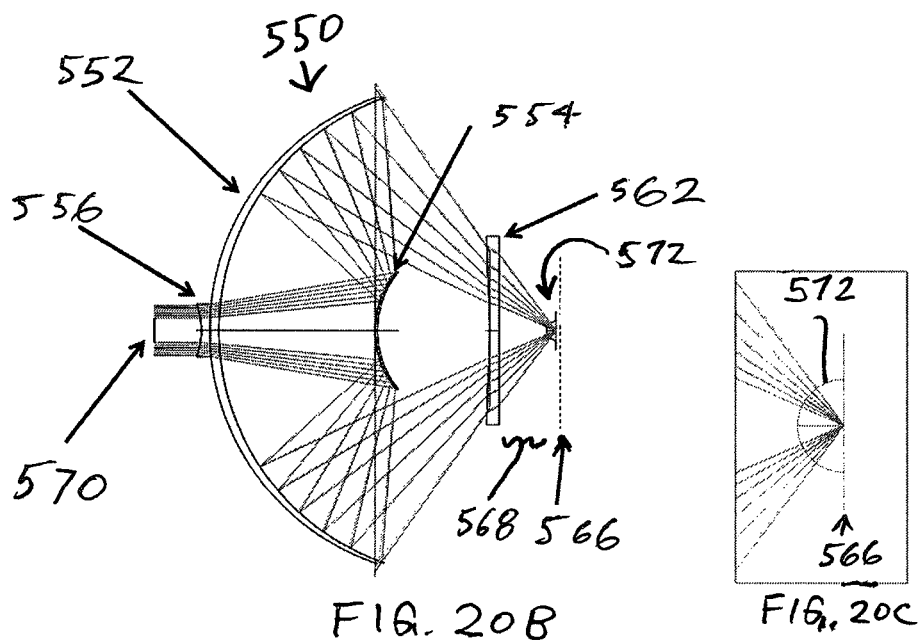

INTERFEROMETRIC SYSTEMS AND METHODS

CROSS-REFERENCE TO RELATED APPLICATIONS

This application is a continuation-in-part of, and claims the benefit of, U.S. utility patent application Ser. No. 12/304,494 filed on Dec. 12, 2008 and entitled "Apparatus and Method for Deep Ultraviolet Microscopy", which is the U.S. national phase of PCT patent application no. PCT/US2007/071003 filed on Jun. 12, 2007 and entitled "Apparatus and Method for Deep Ultraviolet Microscopy", which in turn claims priority to U.S. provisional patent application No. 60/812,912 filed on Jun. 13, 2006 and entitled "Method and Apparatus for Deep Ultraviolet Microscopy", each of which is hereby incorporated by reference herein.

STATEMENT REGARDING FEDERALLY SPONSORED RESEARCH OR DEVELOPMENT

N/A

FIELD OF THE INVENTION

The present invention relates to optical techniques such as optical microscopy and/or interferometry and, more particularly, to such optical techniques that employ light at wavelengths outside of the visible light spectrum.

BACKGROUND OF THE INVENTION

Optical microscopes and interferometry are two examples of optical techniques that are useful in various applications but which suffer from certain limitations as conventionally implemented. With respect to optical microscopes, such devices have numerous applications in both the physical sciences as well as in the life sciences. In semiconductor manufacturing for example, visible light microscopes are used for inspecting semiconductor wafers following many of the several hundred process steps employed to fabricate semiconductor devices. This optical wafer inspection technique has advantages over the use of electron microscopy. In particular, optical microscopy is a non-destructive technique in that it does not involve breaking valuable wafers. Also, optical microscopy does not involve evaporating coating onto the samples, or evacuating the sample chamber, both of which can be time consuming. Further, optical microscopes typically do not cost as much as electron microscopes, and the technical skill level required to operate optical microscopes to obtain high quality micrographs typically need not be as high as that required to operate electron microscopes.

Notwithstanding the advantages of optical microscopes relative to electron microscopes such as those described above, in recent years there has been a significant decline in the sale of optical microscopes. This is partially due to a decline in their utility for semiconductor research and manufacturing, where the minimum feature size for present day devices has decreased to less than 0.5 microns, and in some advanced chip designs to less than 0.1 microns. In particular, because the ability of visible light optical microscopes to discern useful information concerning features of 0.5 microns or less is marginal, electron microscopes have increasingly become the tool of choice in observing such features.

In view of these considerations, and since the resolution of an optical imaging system scales linearly with wavelength, it is desirable to design an optical microscope that utilizes light at shorter wavelengths than light within the visible spectrum. A number of techniques involving shorter-wavelength light have been considered, yet these techniques suffer from various disadvantages. For example, while an optical microscope employing light within the near ultraviolet range (approximately 200 nm<$\lambda$<400 nm) may provide some wavelength advantage over a visible light optical microscope, the difficulties of image display and aberrations in optical components may not justify that advantage.

Also for example, a number of ultraviolet microscopes have been designed for the "soft X-ray" region, particularly at a wavelength of 2.48 nm. This wavelength is useful because of reduced water absorption by biological specimens in the range 2.4-4.4 nm. The radiation source is the six-fold ionized Nitrogen atom, N VII. However, it is difficult energetically to dissociate Nitrogen and then form the $N^{+6}$ ion in an electronically excited state. Indeed, to perform such a process and thereby generate light at the desired wavelength, complicated methods and equipment such as pinched plasma sources and high-powered pulsed lasers are necessary. Further, because the atmosphere substantially absorbs light at the above-mentioned wavelengths, optical microscopes utilizing light at such wavelengths typically must be designed so that the transmission of light occurs within a high vacuum. Implementation of a microscope in a manner such that light is transmitted within a high vacuum, however, can be challenging and costly. Again with respect to the semiconductor industry more particularly, cost-effective, high throughput optical mask inspection below the 32 nm node is on the verge of resolution and practicality limits, and it has been predicted that progression into sub-32 nm half-pitch in 2015 (sub-128 nm at the mask), even if manufacturable at the wafer level with advanced processing techniques, presents a difficult challenge for the photomask industry. To make matters worse from an inspection perspective, the NAND Flash timeline is already at 22 nm (88 nm at the mask), and is predicted to dive into sub 20-nm by 2014. High-throughput semiconductor photomask inspection is essentially optically-driven, but requirements for future technology nodes are about to surpass the capabilities of ArF (193 nm) and KrF (248 nm) technologies. While sources at extreme ultraviolet (EUV) wavelengths (e.g., 13 nm) have been attempted, these options still appear to present a risk of high cost and complications.

For at least these reasons, it would be advantageous if a new optical microscope and/or imaging system, and/or a new interferometer, and/or other optical systems, and/or one or more related methods of performing optical microscopy and/or interferometry and/or other optical techniques could be developed. In at least some embodiments, it would be particularly advantageous if such an improved microscope, imaging system, interferometer, and/or other optical system, and/or method utilized light at one or more wavelengths that were shorter than those of the visible light spectrum, so as to allow for enhanced viewing, probing, and/or measuring of small features, spaces, or distances. Further, in at least some embodiments, it would be particularly advantageous if such an improved microscope, imaging system, interferometer, and/or other system and/or method could be implemented without the need for extremely complicated or costly light sources, and/or could achieve successful operation even without the use of a high vacuum to facilitate the efficient transmission of light.

SUMMARY OF THE INVENTION

The present inventors have recognized that an improved optical microscope, and/or an improved interferometer, and/ or an improved interferometric lithography system (and/or other optical systems and/or related imaging system(s) and/or method(s) of performing optical microscopy, interferometry, interferometric lithography, and/or other optical techniques) suitable for viewing, probing, modifying, or creating many small features can be achieved in at least some embodiments by utilizing the intense, substantially monochromatic and isolated radiation of the atomic Hydrogen resonance line at 121.6 nm (the Hydrogen Lyman-α line) in the deep or vacuum ultraviolet region of the electromagnetic spectrum (e.g., λ<190 nm or λ<185 nm). The present inventors have further recognized that the use of light at this wavelength is advantageous in several regards. More particularly, the present inventors have recognized that there is a narrow, highly transparent "window" in the air absorption spectrum, also precisely at 121.6 nm, such that light emitted at the Hydrogen Lyman-α line from a light source can be effectively transmitted within the optical microscope, interferometer, interferometric lithography system, or other optical system without the need to work in high vacuum. Additionally, the present inventors have recognized that effective light sources and optical components can be developed for giving off, transmitting, and/or processing strong, relatively-monochromatic light at the Hydrogen Lyman-α line.

More particularly, in at least some embodiments the present invention relates to an optical system comprising at least one light source, a lens device, a beam splitter, and a camera device. The at least one light source includes a deep ultraviolet light source configured to generate first light having a wavelength within a window in the deep ultraviolet region of the electromagnetic spectrum within which a local minimum in the absorption coefficient of oxygen occurs, wherein the wavelength is approximately 121.6 nm, and wherein the at least one light source is further configured to generate second light that includes visible light or near-ultraviolet light and that is directed toward a target location. The lens device receives at least a first portion of the generated first light, directs at least some of the first portion of the generated first light toward the target location, receives reflected light from the target location, and directs at least some of the reflected light toward a further location, where at least a part of a light path between the deep ultraviolet light source and the target location is other than at a high vacuum. The beam splitter is positioned between at least two of the deep ultraviolet light source, the lens device and the camera device. The camera device is positioned at one of the further location and an additional location, where the camera device receives at least a second portion of the reflected light, whereby an image is generated by the camera device based upon the second portion of the reflected light. In at least some such embodiments, the optical system is an interferometer.

Additionally, in at least some embodiments, the present invention relates to an interferometric system. The interferometric system includes at least one light source including a deep ultraviolet light source configured to generate first light having a wavelength within a window in the deep ultraviolet region of the electromagnetic spectrum within which a local minimum in the absorption coefficient of oxygen occurs, where the wavelength is approximately 121.6 nm, and where the at least one light source is further configured to generate additional light that includes visible light or near-ultraviolet light and that is directed toward a target location. Also, the interferometric system includes a lens device that receives a first portion of the generated first light and directs the first portion of the generated first light toward the target location, where at least a part of a first light path between the deep ultraviolet light source and the target location is other than at a high vacuum. Additionally, the interferometric system includes a beam splitting device that is positioned between the deep ultraviolet light source and the lens device, where interference occurs between a second portion of the generated first light and either the first portion of the generated first light or reflected light received by lens device from the target location after the first portion of the generated first light is directed toward the target location. In at least some such embodiments, the interferometric system includes an interferometer or an interferometric lithography system.

Also, in at least some embodiments the present invention relates to an apparatus for performing optical microscopy. The apparatus includes a deep ultraviolet light source configured to generate light having a wavelength within a window in the deep ultraviolet region of the electromagnetic spectrum within which a local minimum in the absorption coefficient of Oxygen occurs. Further, the apparatus includes a lens device that receives at least a first portion of the generated light, directs at least some of the first portion of the generated light toward a target location, receives reflected light from the target location, and directs at least some of the reflected light toward a further location. Additionally, the apparatus includes a camera device that is positioned at one of the further location and an additional location, where the camera device receives at least a second portion of the reflected light, whereby an image is generated by the camera device based upon the second portion of the reflected light.

Additionally, in at least some embodiments the present invention relates to a method of performing optical microscopy. The method includes generating light at a light source, wherein a wavelength of the generated light is within a window in the deep ultraviolet region of the electromagnetic spectrum within which a local minimum in the absorption coefficient of Oxygen occurs, the window being at least one of about 1.0 nm and about 2.0 nm in width. The method further includes transmitting the generated light to a target location by way of at least one lens device, and communicating reflected light received from the target location to a further location, where at least a portion of the reflected light is at the wavelength and occurs in response to the transmitting of the generated light to the target location. The method additionally includes producing an image based upon the reflected light.

In at least some embodiments encompassed herein, an apparatus for microscopy includes means for generating light having a wavelength within a window in the deep ultraviolet region of the electromagnetic spectrum, where an absorption coefficient of Oxygen at standard temperature and pressure that corresponds to the first wavelength is less than 25 atm$^{-1}$ cm$^{-1}$. The apparatus additionally includes means for directing at least a first portion of the generated light toward a target region and for directing reflected light received from the target region toward a further location in a substantially collimated manner. The apparatus also includes means for producing an image based upon at least a portion of the reflected light, the image being representative of a feature of a target item positioned at the target region.

Additionally, in at least some embodiments, the present invention relates to a method of performing interferometry. The method includes providing visible light to a target location, and generating additional light at a light source, where a wavelength of the generated additional light is within a window in the deep ultraviolet region of the electromagnetic spectrum within which a local minimum in the absorption coefficient of Oxygen occurs, the window being at least one of about 1.0 nm and about 2.0 nm in width, wherein the wavelength is approximately 121.6 nm. The method additionally includes transmitting a first portion of the generated additional light to the target location by way a beam splitter and at least one lens device, where at least a part of a light path between the light source and the target location is other than at a high vacuum. The method further includes communicating reflected light received from the target location, by way of the at least one lens device and the beam splitter, to a further location at which is positioned a camera system, wherein the reflected light includes at least some of the first portion of the generated additional light. The method also includes further transmitting a second portion of the generated additional light to the camera system, wherein the second portion of the generated additional light reaches the camera system after experiencing reflection at each of the beam splitter and a mirror. The method further includes producing, at the camera system, an image indicative of interference between the reflected light and the second portion of the generated additional light.

BRIEF DESCRIPTION OF THE DRAWINGS

FIG. 6 shows a further exemplary lens arrangement including a solid immersion lens, which can be employed in the optical microscope of FIG. 1;

FIGS. 16A-16B shows exemplary spot diagrams for the interferometer of FIGS. 12-13;

FIG. 19A is a graph and FIGS. 19B-19C are spatial variation diagrams showing example predicted performance results achievable using the interferometric lithography systems of FIGS. 17 and 18; and FIGS. 20A and 20B are schematic diagrams illustrating two alternative embodiments of objective lenses that can be employed in alternate embodiments of any of the optical microscopy, interferometric, interferometric lithography, and other systems encompassed herein, and FIG. 20C provides a detail view of a solid immersion lens (SIL) of the objective lens of FIG. 20B.

DETAILED DESCRIPTION OF THE PREFERRED EMBODIMENT

Figure 1:
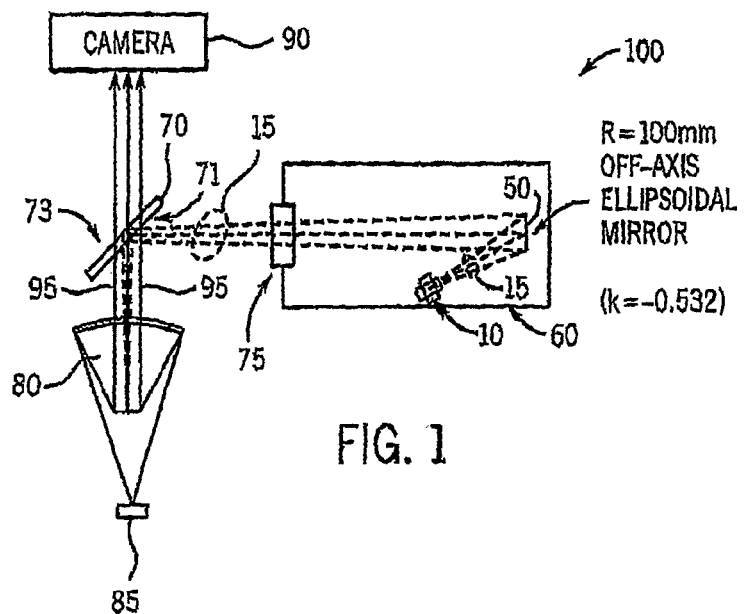
FIG. 1 shows, in simplified schematic form, exemplary components of an optical microscope that utilizes light at the Hydrogen Lyman-α line, in accordance with one embodiment of the present invention.

FIG. 1 illustrates, in simplified schematic form, exemplary components of an optical microscope 100, in accordance with at least one embodiment of the present invention. As will be described in further detail below, the optical microscope 100 operates through the use of light at the Hydrogen Lyman-α line, that is, light at (or approximately at) a wavelength of 121.6 nm. This wavelength is in the "vacuum ultraviolet" and "deep ultraviolet" regions of the electromagnetic spectrum, which generally overlap one another, albeit the vacuum ultraviolet region is generally understood to extend from the region of strong absorption by molecular Oxygen near about 190 nm (or alternatively near about 185 nm) to the "Soft" X-ray region near 20 nm while the deep ultraviolet region is generally understood to extend to wavelengths somewhat higher than 190 nm (e.g., up to nearly 200 (e.g., 193) or 250 (e.g., 248) nm. Further as will be described below, utilization of light at the Hydrogen Lyman-α line should provide about a four-fold increase in the resolution achievable by the optical microscope 100 relative to conventional optical microscopes, and thereby extend the usefulness of optical microscopy to a variety of applications.

As shown in FIG. 1, the optical microscope 100 in the present embodiment includes a source module 60, a beam splitter 70, an objective lens 80, and a camera module 90. Within the source module 60, light at the Hydrogen Lyman-α line is generated by way of a microwave-driven gas-discharge light source 10, which is described in further detail with respect to FIG. 9. Further as shown, light 15 emanating from the light source 10 is reimaged by an ellipsoidal mirror 50, which also is positioned within the source module 60. The ellipsoidal mirror 50 in turn reflects the light 15 out of the source module 60 and toward the beam splitter 70. In some embodiments including the present embodiment, to pass out of the source module 60 the light 15 passes through an optical window 75. By employing such a window, the interior of the source module 60 can be substantially sealed off from the outside atmosphere.

Upon the light 15 reaching the beam splitter 70, the beam splitter reflects a fraction of the incoming light 15 to the objective lens 80. Although the beam splitter 70 can take various forms, in the present embodiment it is a $MgF_2$ beam splitter that includes a first substantially planar surface 71 oriented at approximately 45 degrees relative to the path of the light 15 emanating towards it, such that the reflected light proceeding away from the beam splitter proceeds in a direction that is approximately 90 degrees relative to the incoming light. In at least some embodiments, the surface 71 can have deposited on it a thin-film coating that allows a fraction of the light 15 to be reflected to the objective lens 80 and a second fraction to be transmitted.

Figure 2:
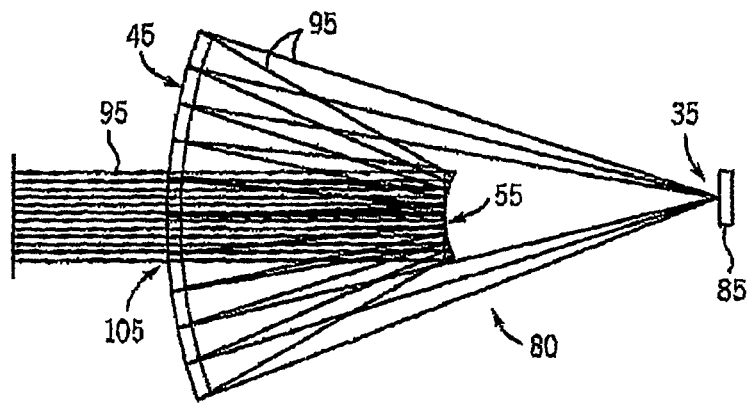
FIG. 2 shows in further detail an objective lens employed in the optical microscope of FIG. 1, in accordance with one embodiment of the present invention.
Figures 3A, 3B, 3C, 3D:
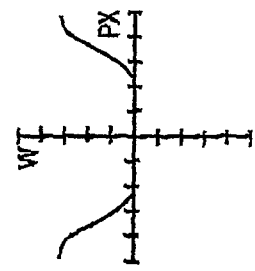
FIGS. 3A-3D show exemplary wavefans for the objective lens of FIGS. 1-2.
Figure 4A:
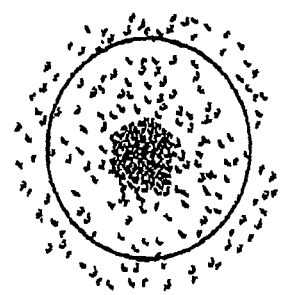
FIGS. 4A-4B shows exemplary spot diagrams for the objective lens of FIGS. 1-2.
Figure 4B:
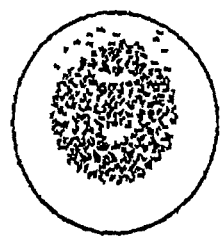

As described in further detail with respect to FIG. 2, the objective lens 80 upon receiving the reflected light from the beam splitter 70 then directs that light at a target 85, which can be any of a variety of structures, materials, etc. (e.g., semiconductor wafers or biological cells). Depending upon the target 85, typically some or most (or even all) of the light incident upon the target is reflected off of the target back toward the objective lens 80. This light reflected off of the target 85 and received by the objective lens 80 then is directed back to the beam splitter 70 by the objective lens as returning light 95. Due to the design of the beam splitter 70 and any additional thin-film coating provided on the surface 71, a fraction of the returning light 95 proceeds through the beam splitter (instead of being reflected by the beam splitter) toward the camera module 90.

The returning light 95 proceeding to the camera module 90 is collimated or substantially collimated such that it is capable of being used for imaging purposes. Thus, upon receiving the returning light 95, the camera module in turn is capable of receiving and observing/storing the light and generating images or imaging information indicative of one or more features of the target 85 based upon that light. Alternatively, the returning light 95 can be slowly converging in order to form an image inside the camera module 90. Additionally, in at least some embodiments, a second substantially-planar surface 73 of the beam splitter 70 (on the opposite side of the beam splitter relative to the first substantially-planar surface 71) can also have an anti-reflection film deposited thereon, so as to limit ghost images from reaching the camera module 90.

In use, the optical microscope 100 operates as follows. First, before the providing of any light from the light source 10 at the Hydrogen Lyman-α line, an operator will first locate the feature of interest (e.g., the target 85 or a portion thereof) using a visible light source (e.g., 400 nm<λ<700 nm), which is not shown in FIG. 1. Upon locating the feature of interest, the operator then switches on the light source 10 (and switches off the visible light source). At that point, the light 15 is directed from the light source 10 to the target 85 by way of the beam splitter 70, mirror 50, etc., which in turn results in the providing of the returning light 95 from the target to the camera module 90. The operator then is able to view a high resolution image obtained by way of the camera module 90 on a video display monitor, which can be considered to form part of the camera module or alternatively be separate from it (e.g., in the form of a personal computer coupled to the camera module by way of a dedicated communication link, a network link, the Internet, wireless communications, or otherwise). Also, the images can be printed in hardcopy form by way of the camera module or otherwise.

Referring additionally to FIG. 2, the objective lens 80 of FIG. 1 is shown in somewhat more detail in relation to the target 85. FIG. 2 particularly illustrates exemplary paths of the returning light 95 reflected off of the target 85, which can be understood as being positioned at a focal point 35. As shown, the central portion of the beam of the returning light 95 provided from the target 85 is occluded from the first spherical mirror 45 by the second spherical mirror 55. The portion of the returning light 95 that reaches the first spherical mirror 45 is reflected by that mirror back to the second mirror 55, which in turn reflects the light out of the objective lens 80 by way of an orifice 105 formed within the first spherical mirror (toward the beam splitter 70 and ultimately the camera module 90). The light emanating from out of the objective lens 80 by way of the orifice 105 preferably is collimated, or substantially collimated. Although not shown in detail, the light 15 from the light source 10 entering the objective lens 80 takes paths that are the opposite or substantially the opposite of those shown. More particularly, upon entering the objective lens 80 by way of the orifice 105, the light 15 is reflected off of the second spherical mirror 55 (which constitutes the pupil of the lens) back toward the first spherical mirror 45, which in turn reflects the light toward the target 85. Although it is not necessarily the case, preferably the objective lens 80, upon receiving the light 15 from the light source, produces uniform Kohler illumination for the target 85 (albeit, more important than producing uniform Kohler illumination is that an accurate camera module 90 be employed in the system).

The objective lens 80 in the present embodiment is a simple Schwartzschild configuration lens having first and second spherical mirrors 45 and 55, respectively, such as that described in "Schwartzschild Objective for Soft X-rays" by I. A. Arioukov and K. M. Krymski (Opt. Eng. 39 (8), 2163-2170 (2000)), which is hereby incorporated by reference herein. In the present embodiment, the objective lens 80 is optimized for an infinite image conjugate in Zemax® lens design software available from ZEMAX Development Corporation of Bellevue, Wash. In particular, the first spherical mirror 45 has a clear aperture diameter of 42.26 mm. For an operation wavelength of 121.6 nm, a numerical aperture of slightly greater than 0.3 is achieved with reasonable field performance out to a field diameter of about 300 μm. Additional details regarding the design are provided in Table 1.

TABLE 1

OBJECTIVE LENS PRESCRIPTION

| Surface/ Reference Numeral | Radius (mm) | Thickness to next element (mm) | Description |
| --- | --- | --- | --- |
| Beam Splitter/70 or Camera Module/90 | Infinity | Infinity | Object is at infinity (reversed configuration for design) |
| Second Spherical Mirror/55 | 20.00 | −32.33 | Second spherical mirror that also functions as the stop. |
| First Spherical Mirror/45 | 52.36 | 68.62 | First spherical mirror |
| Target/85 | Infinity | 0 | Image |

Further exemplary characteristics of the objective lens 80 of FIGS. 1-2 are shown in FIGS. 3A-3D and 4A-4B. More particularly, FIGS. 3A-3D show exemplary wavefans for the objective lens 80, where the lines shown represent the departure of the ideal focusing beam from the real beam as measured at the pupil (the second spherical mirror 55) of the objective lens (with an assumed wavelength λ=121.6 nm). The maximum vertical sale for the wavefans is +/−0.2 wavelengths. The horizontal axes correspond to the dimension across the center of the pupil, from edge to edge (e.g., either the x-axis or the y-axis). The wavefans of FIGS. 3A and 3B, which are respectively plotted versus x-direction and y-direction orthogonal measurement lines across the center of the pupil, correspond to the lens performance of a point centered (0.0000 degrees) in the field of the target 85. The wavefans of FIGS. 3C and 3D, which are respectively plotted versus x-direction and y-direction orthogonal measurement lines across the center of the pupil, correspond to the lens performance of a point at the edge (0.5000 degrees or 0.141 mm) of the field of the target 85. As for FIGS. 4A-4B, these show exemplary spot diagrams for the objective lens 80. In particular, the Airy disk diameter (ideal diffraction-limited diameter) is indicated by the circles. The points represent the intersection of the geometric rays, as traced through the system from the target. The spot diagram of FIG. 4A in particular corresponds to the lens performance of a point centered (0.0000 degrees) in the field of the target 85. The spot diagram of FIG. 4B by comparison corresponds to the lens performance of a point at the edge (0.5000 degrees or 0.141 mm) of the field of the target 85.

Additionally it should be noted that, in at least some embodiments, a thin-film coating can be provided on the mirrors 45, 55, in order to enhance mirror reflectivity. One such film is a CVD-coated SiC material, which has between 40% to 50% reflectivity at $\lambda=121.6$ nm (e.g., reflectivity above 45% in the vacuum ultraviolet region of interest) and exhibits a refractive index of 2.66 leading to a 20% reflectivity for visible light, as described in an article entitled "Ultraviolet reflectance of AlN, diamond-like carbon, and SiC thin films," by M. David, et. al., Appl. Phys. Lett., 57 (11), pp. 1093-1095 (1990), which also is hereby incorporated by reference herein.

Notwithstanding the above description of the objective lens 80, a variety of other lens designs can also be employed depending upon the embodiment, and the present invention is intended to encompass the use of any of a variety of different lenses (including sets of multiple lenses). In embodiments similar to that discussed above in which both visible light and light at the Hydrogen Lyman-α line are used, the large variation in wavelength between the visible light and the light at the Hydrogen Lyman-α line makes it undesirable to utilize refractive optics due to chromatic aberration. Given that to be the case, reflective objective lens designs such as that described above are preferred for such embodiments. Other such reflective lens designs can also be employed including, for example, lens designs employing spherical mirrors in which the Schwartzschild conditions are relaxed (and in which no refracting components or compensating lenses are employed), as described in an article entitled "Reflecting microscopes with spherical mirrors" by K. P. Norris et. al. found in J. Opt. Soc. Am., 41, 111 (1951), which is hereby incorporated by reference herein (the numerical aperture for the microscope shown in that article employing such lenses was approximately 0.65).

In further embodiments, non-spherical mirrors can be utilized in the optical microscope, for example, as shown in an article entitled "Reflecting microscope objectives with non-spherical mirrors" by S. Miyata found in J. Opt. Soc. Am, 42, 431 (1952), which is hereby incorporated by reference herein (in this example, the aplanatic objective lens was free of spherical aberration and coma). Also, notwithstanding the above description regarding the objective lens 80, in some alternate embodiments additional improvements to Schwartzschild mirrors can be employed, as described in articles by D. S. Grey found in the Journal of the Optical Society of America (J. Opt. Soc. Am.) entitled "A new series of microscope objectives: I. Catadioptric Newtonian Systems", 39, 719 (1949) (co-author Paul Lee), "A new series of microscope objectives: II. Preliminary investigation of catadioptric Schwarzschild systems" 39, 723 (1949), and "New series of microscope objectives: III. Ultraviolet objectives of intermediate numerical aperture" 40, 283 (1950), which also are hereby incorporated by reference herein. Still in further embodiments, other types of mirrors or mirror assemblies such as Cassegrain reflectors can instead (or in addition) be utilized.

Figure 5A:
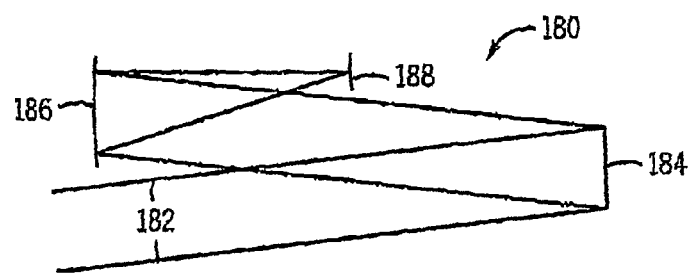
FIGS. 5A-5B show, in further detail, first and second additional objective lenses that can be employed in the optical microscope of FIG. 1.
Figure 5B:
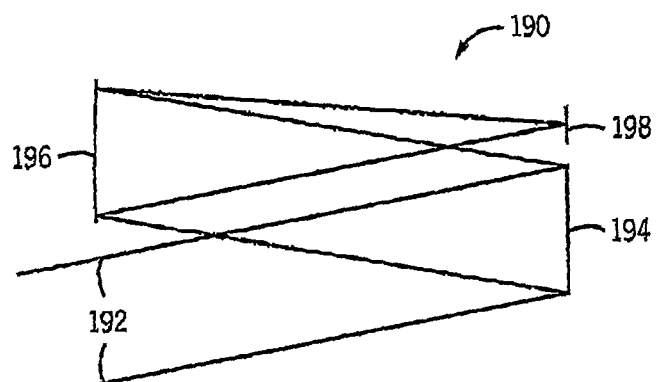

Further in this regard, FIGS. 5A and 5B illustrate first and second additional embodiments for objective lenses 180 and 190, respectively, which are described in additional detail at pages 200 and 202, respectively, of "Reflective Optics" by Dietrich Korsch (Academic Press, San Diego, 1991), which is hereby incorporated by reference herein. As shown, the objective lens 180 is a reflective analog of a Schmidt telescope in which incoming light rays 182 (e.g., light from the light source 10) are first reflected off of a primary correction (entrance pupil) mirror 184 and then subsequently reflected a second time off of a spherical secondary mirror 186, which focuses the rays at a focal point 188 (albeit in this example it should be understood that the path(s) of the light rays are not the same as the paths from a light source in a Kohler configuration). Light reflected off of a target (such as the target 85 of FIG. 1) located at the focal point 188 can return along a path that is effectively the reverse of that followed by the incoming rays 182, after which the light is directed toward a camera module (e.g., by way of the beam splitter 70). As for the objective lens 190, it is an aplanatic, flat-field two-mirror telescope with a primary corrector. More particularly as shown, incoming light rays 192 are first received at and reflected by a primary corrector mirror 194, which reflects the light toward a secondary mirror 196, which in this example is of an oblate ellipsoid shape. The secondary mirror 196 in turn reflects and focuses the light toward a focal point 198, at which can be a target (and where, again, the light ray paths are not identical to those of a Kohler configuration). Light reflected off of the target can return along a path that is effectively the reverse of that followed by the incoming rays 182, after which the light is directed toward a camera module.

Although the above embodiments employing visible light in addition to light at the Hydrogen Lyman-α line envision the use of only reflective objective lens designs, it should be further noted that in other alternate embodiments it is possible to utilize both reflective and refractive optics. For example, several of the above-referenced reflective microscope designs described in the literature were intended for use with an illumination source being the Hg 253.7 nm emission line, in the near ultraviolet spectral region where air is transparent. Quartz is also transparent in this region and consequently a microscope design comprising both reflective and refractive optics is possible. Further, in still other alternate embodiments, it is not necessary to utilize a visible light source at all. For example, the use of visible emissions from a Hydrogen/Helium discharge will obviate the need for a separate visible light source. This visible emission from the gas-discharge is mainly due to Hydrogen Balmer lines and electron-ion recombination emission in the gas-discharge region.

Additional lens systems having both reflective and refractive optical components can be formed through the use of a solid immersion lens (SIL) (or possibly several such lenses). For example, one such system 200, which is shown in FIG. 6, incorporates both a SIL 199 in combination with an objective lens such as the objective lens 80 of FIG. 2 having both the first and second spherical mirrors 45 and 55, respectively. As shown, the SIL 199 in this embodiment is positioned proximate the focal point 35 at which is located the target 85. SILs such as the SIL 199 can be made from LiF or $MgF_2$. A SIL composed of an image-centric LiF hemisphere in particular can increase the effective numerical aperture of the system from 0.3 to 0.486. Other reflective microscope designs with higher numerical aperture can also, when augmented with a SIL, produce numerical apertures greater than 1.0.

As already noted, the optical microscope 100 shown in FIG. 1 employs light at the Hydrogen Lyman-α line, that is, light having a wavelength of 121.6 nm (or substantially or approximately 121.6 nm). The use of light at this wavelength is advantageous in several regards. First, light at the Hydrogen Lyman-α line is fairly easily transmissible through air without a vacuum, such that the optical microscope 100 can be operated without any need for a high-vacuum light path. More particularly, strong absorption of light by molecular Oxygen ($O_2$) generally occurs for wavelengths below about 190 nm, such that air generally is opaque in the deep ultraviolet region of the electromagnetic spectrum. However, by a coincidence of Nature, there exists a narrow, highly transparent "window" in the air absorption spectrum that coincides with the Hydrogen Lyman-α line. Variation in the absorption of light by Oxygen at and around the Hydrogen Lyman-α line is shown in FIGS. 7 and 8, which respectively show the absorption spectrum in Oxygen between 125 nm and about 180 nm, and the absorption spectrum in Oxygen between 105 nm and about 135 nm, respectively.

Figure 7:
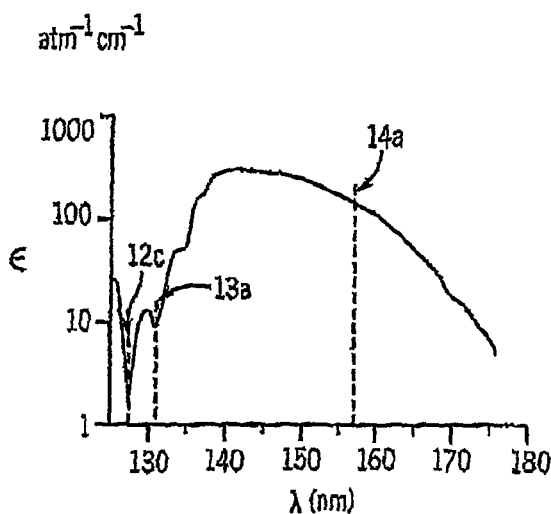
FIG. 7 is the absorption spectrum of Oxygen between 125 nm and about 180 nm.
Figure 8:
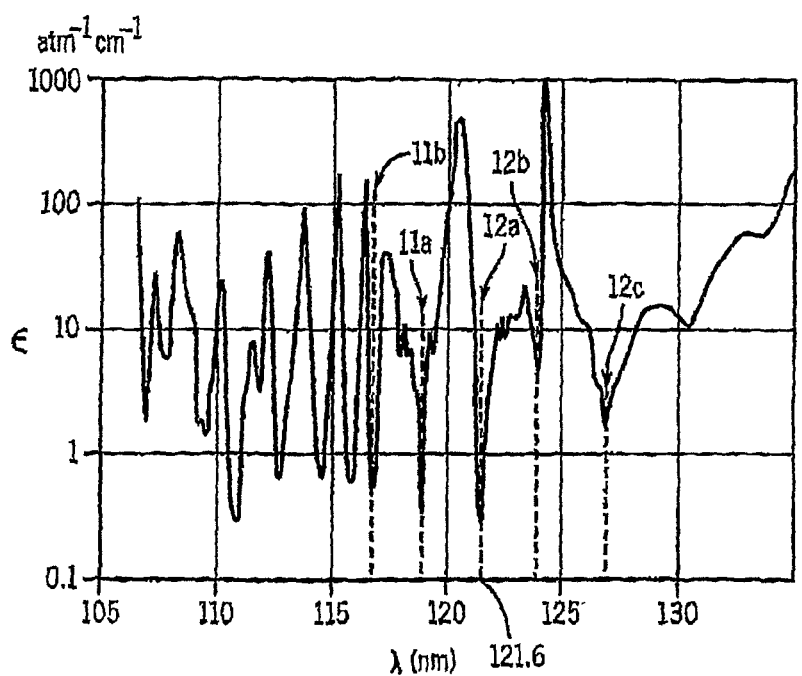
FIG. 8 is the absorption spectrum in Oxygen between 105 nm and about 135 nm, showing a transmission "window" at 121.6 nm.

More particularly as shown in FIGS. 7 and 8, the absorption coefficient of Oxygen with respect to light having wavelength(s) at or near 121.6 nm is particularly low in comparison with the absorption coefficients for light at essentially all wavelengths longer than 121.6 nm, up to at least about 180 nm. Further as shown particularly in FIG. 8, at standard temperature and pressure, the absorption coefficient of Oxygen ε (in $atm^{-1}\ cm^{-1}$) has a local minimum at the Hydrogen Lyman-α line ($\lambda$=121.6 nm), and the absorption coefficient remains less than 25 $\mu m^{-1}\ cm^{-1}$ within a window encompassing the Hydrogen Lyman-α line that is approximately 1 to 2 nm (or even slightly larger) in width. The absorption coefficient of Oxygen ε for light at 121.6 nm specifically is about 0.3 $atm^{-1}\ cm^{-1}$, as indicated by a location 12a of FIG. 8, which is one to three orders of magnitude less than the absorption coefficients for light at other wavelengths between this window and 175 nm.

Because of this window in the Oxygen (and consequently, atmospheric air) spectrum for light at the Hydrogen Lyman-α line, for path lengths of a few centimeters in air, at atmospheric pressure, transmission of light at the Hydrogen Lyman-α line exceeds 50%. For example, if light at 121.6 nm having an absorption coefficient of 0.3 $atm^{-1}cm^{-1}$ is transmitted over a 2 cm distance, the light will only experience about 12% absorption, such that 88% of the light will be transmitted over such transmission path. This is in contrast to the absorption associated with light having a wavelength of, for example, 157 nm (see arrow 14a of FIG. 7), in which nearly total absorption occurs over a transmission path of less than 1 mm as a result of the high absorption coefficient (about 200 $atm^{-1}cm^{-1}$). Relatedly, for a 50% reduction of absorption of radiation in dry air at one atmosphere, the light path is 110 mm, and a light path of 10 mm in dry air produces only 6% absorption. By contrast, absorption at 157 nm (the wavelength of the $F_2$ laser) is up to three orders of magnitude higher.

Table 2 shows in more detail the path length in air required at various pressures for a fifty percent absorption of radiation, for two different absorption coefficients: $\epsilon_{121.6}$=0.3 $atm^{-1}\ cm^{-1}$, and $\epsilon_{150.0}$=200 $atm^{-1}\ cm^{-1}$. From this information, it is apparent that the use of light at the Hydrogen Lyman-α line allows for much more efficient transmission of the light through the air than is afforded when using light having a wavelength near 150 nm.

TABLE 2

MAXIMUM PATH LENGTHS WITHIN AIR ALLOWING FOR 50% TRANSMISSION OF LIGHT AT 121.6 NM AND 150 NM

| P (atm.) | Light Path (cm) @ 121.6 nm | Light path (cm) @ 150.0 nm |
|---|---|---|
| 1.00 | 11.0 | 0.0165 |
| 0.50 | 22.0 | 0.033 |
| 0.10 | 110 | 0.165 |
| 0.050 | 220 | 0.330 |
| 0.010 | 1100 | 1.65 |
| 0.0010 | 11000 | 16.5 |

In addition to the above, a pure Nitrogen gas ($N_2$) environment experimentally produces only approximately 0.3% absorption per 10 mm of path length for Hydrogen Lyman-α light. That is, transmission of light at the Hydrogen Lyman-α line within an $N_2$ environment does not significantly increase the level of absorption that occurs, by comparison with transmission of such light through air at atmospheric pressure. Thus, the combination of narrow line emission, low absorption in dry air and negligible absorption in an $N_2$ environment is also advantageous and, as discussed further below, is employed in at least some of the optical microscopy and interferometric systems encompassed herein. That is, although some of the embodiments of systems encompassed herein are configured to transmit Hydrogen Lyman-α light at least partly within air at atmospheric pressure, additional embodiments of systems encompassed herein are configured to transmit Hydrogen Lyman-α light at least partly within an $N_2$ environment instead of, or in addition to, transmission of the Hydrogen Lyman-α light through air at atmospheric pressure.

Although the use of light at the Hydrogen Lyman-α line having a wavelength of 121.6 nm is particularly advantageous for transmission purposes, FIGS. 7 and 8 additionally illustrate that there are several other local minima in terms of absorption that occur proximate the Hydrogen Lyman-α line, within a region extending below about 135 nm. For example, additional local minima also occur at locations 11a, 11b, 12b, 12c, and 13a, all of which are within about 10 nm of the Hydrogen Lyman-α line. Therefore, although the above-described embodiments of the invention primarily envision the use of light at the Hydrogen Lyman-α line, it is possible that alternate embodiments of the invention would utilize light at other wavelengths instead of or in addition to light at the Hydrogen Lyman-α line, and particularly light at wavelengths corresponding to the aforementioned locations at which absorption minima occur.

In addition to coinciding with a window in the Oxygen absorption spectrum, the use of light at the Hydrogen Lyman-α line is also advantageous in that it can be fairly easily generated by way of any of a variety of different light source mechanisms. It is well known that microwave excitation is effective in creating gaseous discharge emissions, for example, as shown in "Microwave Breakdown in Gases" by A. D. MacDonald (John Wiley, New York, 1966), which is hereby incorporated by reference herein. Further for example, small, microwave driven Hydrogen Lyman-α line light sources (and the Deuterium analog) have been fabricated to study chemical kinetics, as described by an article entitled "Quenching and Radiative Lifetimes for NH ($b^1\epsilon^+$, $v^1$=0)" by B. Gelernt and S. V. Filseth in Chem. Phys. Lett. 36, 238 (1975), which is hereby incorporated by reference herein.

Figure 9:
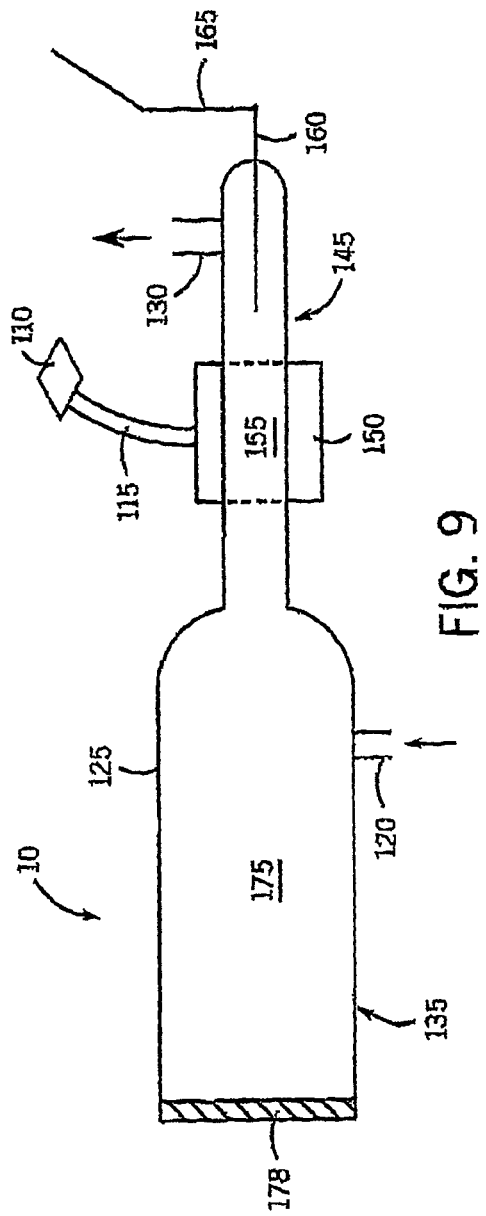
FIG. 9 shows in schematic form one exemplary design of a light source capable of producing light at the Hydrogen Lyman-α line that can be employed in the optical microscope of FIG. 1, in accordance with one embodiment of the present invention.

Turning to FIG. 9, one exemplary configuration of the light source 10 of FIG. 1 that is capable of producing light at the Hydrogen Lyman-α line in accordance with one embodiment of the present invention is shown to involve a microwave-excited gas discharge process. In this exemplary embodiment, the microwave energy is provided by a microwave source 110 (or, in alternate embodiments, by some other excitation source). The Hydrogen Lyman-α line is at a much shorter wavelength than other Hydrogen emissions or Helium discharge emissions (above the LiF cut-off), and background emission is avoided if Helium is used as a diluent gas in the light source, as discussed in "Vacuum Ultraviolet Spectroscopy" by Zaidel & Shreider, pp. 2-20, Ann Arbor-Humphrey Science Publishers, (1970), which is hereby incorporated by reference herein. Thus, in the present embodiment, a $H_2$/He mixture is introduced via a gas inlet 120 into a housing 125 of the light source 10 and subsequently exits the housing via a gas outlet 130. It can be desirable to have a mixture in which the $H_2$ component is below the flammability limit; however, mixtures with higher concentrations of Hydrogen can also be utilized.

Further as shown, the housing 125 in the present embodiment is a substantially elongated structure of tubular cross-section, where about a first half 135 of the housing is of a larger diameter and a second half 145 of the housing is of a smaller diameter. Additionally, the housing 125 in the present embodiment can be fabricated from quartz or other suitable, non-electrically-conductive material, and in other embodiments can be made from other materials as well. To produce flow of the $H_2$/He mixture through the housing 125 and out the outlet 130, a low capacity mechanical pump (not shown) is further attached to the outlet. The $H_2$/He mixture within the housing 125 is typically desirably maintained at a sub-atmospheric pressure within an interior 175 of the housing. To regulate the pressure within the interior 175, a needle valve (not shown) is also attached to the gas inlet 120 and, by way of a controller (or other mechanism), the operation of the mechanical pump is controlled based upon the information from the needle valve so as to control and regulate the sub-atmospheric pressure in the housing 125.

Additionally as shown, a cylindrical (annular) microwave cavity 150 (such as a quarter-wave Evenson Cavity) concentrically surrounds a discharge region 155 of the second half 145 of the housing 125. Power from the microwave source 110 is supplied to the microwave cavity 150 by way of a waveguide conduit 115. To facilitate initial gas breakdown (as may not always automatically occur) and thereby field ionize the gas mixture components within the interior 175 of the housing 125, a high-voltage pulse through an electrode 160 is also provided at the outer end of the second half 145 of the housing 125 as shown. The electrode 160 is connected to a high-voltage source (not shown) through an electrical lead (or leads) 165. Optimization of the light source 10 depends on various factors, which can be varied depending upon the embodiment, including mixture composition, microwave frequency and power, dimensions of the discharge region 155, gas pressure, and cavity tuning.

Figure 10:
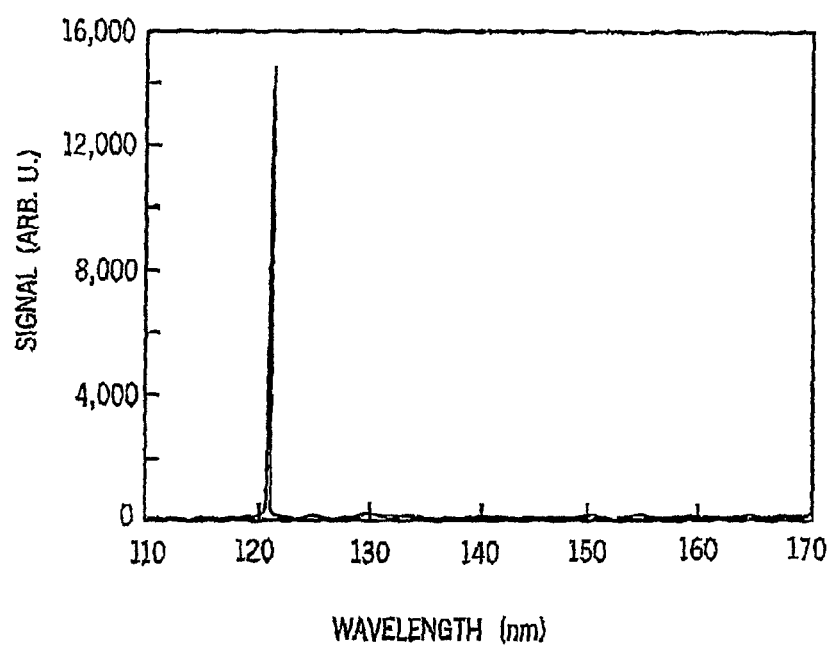
FIG. 10 is the emission spectrum of a Hydrogen-discharge light source such as that of FIG. 9, between about 110 nm and 170 nm.

Once the gas mixture within the interior 175 is appropriately ionized, and microwave energy is communicated to the discharge region 155 by way of the microwave source 110, the waveguide conduit 115 and the microwave cavity 150, a gas discharge occurs in which the Hydrogen portion of the gas mixture emits light at the Hydrogen Lyman-α line. The Hydrogen Lyman-α line at 121.6 nm is a high-intensity source, and more particularly, is actually a spectroscopic doublet, where the two equal intensity, nearly degenerate components have a separation of only 0.0005 nm so as to result in essentially a monochromatic light source. FIG. 10 shows the emission spectrum of a Hydrogen discharge between 110 nm and 170 nm to include the Hydrogen Lyman-α line at 121.6 nm, as can be found in an article entitled "Prospects for photolithography at 121 nm" by Lieberman et al. in J. Vac. Sci. Technol. B, 20 No. 6 November/December 2002, which is hereby incorporated by reference herein. It should be noted that the Hydrogen Lyman-α line light output is characterized by an extremely narrow peak with negligible background near the peak wavelength. It should also be noted that the next line in the Lyman series, which is the Hydrogen Lyman-β line, occurs at 102.6 nm. Although there is commonly some visible light that occurs from the Balmer series (364.6 nm to 656.3 nm), the Balmer light can be filtered with a simple solar-blind detector.

It should further be noted that, in the present embodiment, the light source 10 is capable of being varied in its power output (e.g., it can provide a higher-level power output, and therefore a more intense Hydrogen Lyman-α emission). Depending upon the embodiment, the light output from the light source 10 can be pulsed, but need not be pulsed (for example, the light output can instead be continuous). Depending on the lamp power, frequency and pressure, broadening of the Hydrogen Lyman-α light doublet will vary. The doublet separation and the Doppler width are comparable for low pressure lamps on the order of $10^{-4}$ nm. Notwithstanding the above description, a variety of other Hydrogen Lyman-α sources can be fabricated and utilized for different embodiments of the present invention (for example, a light source driven by a Gunn diode microwave chip or other excitation source). While microwave excitation can be effective in creating gaseous discharge emissions, the present invention is intended to encompass a variety of types of excitation and not necessarily be limited to microwave excitation.

Additionally, although the above description suggests that the light emanating from the light source 10 is exactly at the Hydrogen Lyman-α line, this is not to say that the light source 10 necessarily will be limited to emitting light at the wavelength of the Hydrogen Lyman-α line, 121.6 nm. Rather, the present invention is intended to encompass various embodiments in which all or a substantial proportion of light generated by the light source is within (or concentrated at) a window in the deep ultraviolet region of the electromagnetic spectrum at which the absorption coefficient of Oxygen is sufficiently low so as to make transmission of the light feasible in the absence of a high vacuum. Thus, while some embodiments of the invention employ light that is only exactly (or substantially exactly) at the wavelength of the Hydrogen Lyman-α line, 121.6 nm, other embodiments of the invention generate light within a window or small range of wavelengths about the wavelength of the Hydrogen Lyman-α line.

For example, in some embodiments, the light source generates light within a window that is at least one of about 1.0 nm and about 2.0 nm in width and encompasses the wavelength of the Hydrogen Lyman-α line, for example, light at wavelengths ranging approximately from 121.0 to 122.0 nm or from 121.1 to 122.1 nm, or from 120.5 to 122.5 or from 120.6 to 122.6. In still further embodiments, the window can be 4 nm in size, e.g., +/−2 nm on either side of 121.6 nm, or 8 nm in size, e.g., +/−4 nm on either side of 121.6 nm, etc. Additionally as shown above, several other local minima in the absorption coefficient of Oxygen occur at other wavelengths within the vacuum ultraviolet region proximate the Hydrogen Lyman-α line and so, in further embodiments, one or more light sources are employed to generate light at one or more of these other wavelengths in addition to or instead of at the wavelength of the Hydrogen Lyman-α line, and/or within windows about these wavelengths in addition to or instead of at the wavelength of the Hydrogen Lyman-α line.

Still referring to FIG. 9 and additionally to FIG. 1, it should be further appreciated that the light generated within the interior 175 then proceeds out of the housing 125 by way of an optical window 178 located at the outer end of the first half 135 of the housing, after which it is directed toward the mirror 50 and ultimately to the objective lens 80. In the present embodiment, the optical window 178 is about 0.5 to about 5 mm in thickness, and is securely attached to the remainder of the housing 125, so as to effectively seal the interior 175 from regions exterior to the housing. Preferably, the optical window 178 is placed several centimeters from the discharge region 155 to prevent deterioration of window transmission from ion bombardment. Use of the window 178 makes it possible to control the gas pressure within the interior 175 and particularly within the discharge region 155, and prevents contamination from the light source 10 from entering the rest of the microscope.

Although the present embodiment shows the optical microscope 100 as including both the window 80 of the light source 10 and also the window 75 of the source module 60 of FIG. 1, it will be understood that in some sense the two windows are duplicative and, consequently, in alternate embodiments only one of those two windows will be present (for example, the source module 60 need not be sealed in some embodiments). With respect to the transmittive materials used as the optical windows 75 and 178 (and possibly for other components of the optical microscope 100 as well), high quality components can be fabricated from polished LiF or, alternatively, $MgF_2$. $CaF_2$ is a further possible alternative, but exhibits only poor transmission (e.g., less than 5%). Also, in some embodiments, two or more of these and/or other materials can be employed. In selecting among these materials, it can be noted that the theoretical absorption edge for LiF is approximately 105 nm, and for $MgF_2$ it is near 115 nm. $MgF_2$ is far less hygroscopic than LiF. In the embodiments described herein, including those of FIGS. 1 and 12, it is possible for one or more components to be made of one of the aforementioned materials (e.g., LiF) while one or more other components are made of another of the aforementioned materials (e.g., $MgF_2$).

Figure 11:
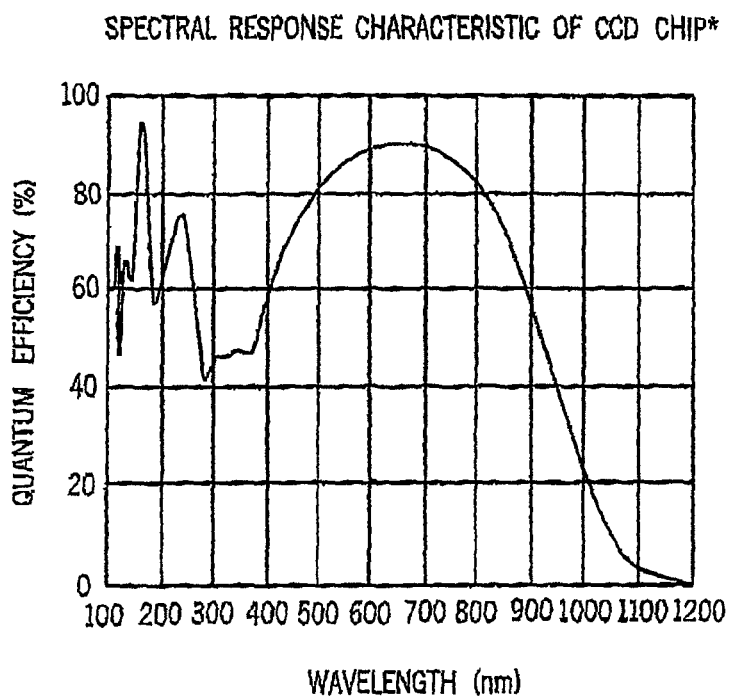
FIG. 11 shows a typical spectral response characteristic of a CCD chip, such as used in the Hamamatsu C8000-10 vacuum ultraviolet camera system, as can be employed in the optical microscope of FIG. 1 in one embodiment of the present invention.

As for the camera module 90, it can take a variety of forms depending upon the embodiment so long as the camera module is capable of receiving and sensing/detecting light at (and around) the Hydrogen Lyman-α line (e.g., at λ=121.6 nm) and generating images based thereupon. In at least some embodiments, the camera module 90 can be a charge coupled device (CCD) camera. For example, one exemplary CCD camera that is sensitive to light at the Hydrogen Lyman-α line and thus can be employed in certain embodiments as the camera module 90 is the Hamamatsu C8000-10, available from Hamamatsu Photonics, K.K., of Hamamatsu City, Japan. That camera's spectral sensitivity is shown in FIG. 11. The pixel size of this camera is 14 μm, such that in at least some embodiments, the magnification of the camera module is 60. Also, in some embodiments, such a magnification can be achieved by altering the design of the Schwarzschild objective lens 80 slightly (yielding this magnification between the object and image), without adding any additional optical components.

Depending upon the embodiment, the camera module 90 is capable of a variety of imaging operations, image processing operations and other operations after receiving and sensing/detecting. In some embodiments, the camera module 90 records imaging information on film that is then processed externally by a third party, or more immediately by the camera module itself. In other embodiments, the camera module 90 stores imaging information on memory within or associated with the camera module. This imaging information can, in at least some embodiments, be stored digitally. Further, in some embodiments, the camera module is capable of performing various digital processing operations upon the imaging information, as well as capable of transmitting the processed (or unprocessed) imaging information to other devices (e.g., computer systems) associated with or remote from the camera module. Such transmission can occur, in at least some embodiments, by various network communication links or even via the internet or the World Wide Web, via hardwired or wireless communication links. In some embodiments, the camera module itself is capable of displaying (e.g., on a video screen or monitor) the images, and/or capable of printing hardcopies of images.

Figure 12:
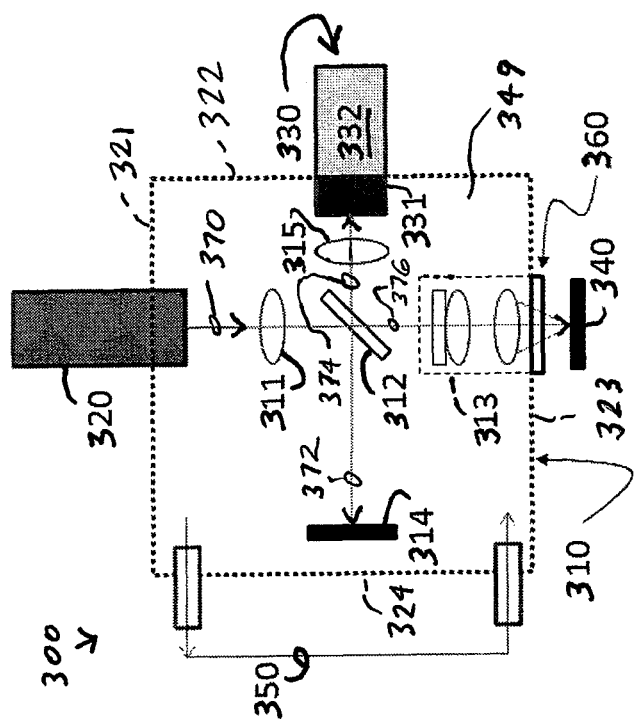
FIG. 12 shows, in simplified schematic form, exemplary components of an interferometer utilizing light at the Hydrogen Lyman-α line, in accordance with one embodiment of the present invention.

Turning next to FIG. 12, in at least some embodiments the present invention also relates to interferometric systems and related methods. FIG. 12 particularly illustrates in schematic form one example interferometer 300 that can be employed to perform, among other things, ultra-high resolution mapping of material properties in thin films, substrates, and semiconductors. As was the case with the optical microscope 100 discussed above, the interferometer 300 takes advantage of the natural coincidence that the Hydrogen Lyman-α line at 121.6 nm in the deep or vacuum ultraviolet region of the electromagnetic spectrum falls within the narrow, highly transparent "window" in the air absorption spectrum (also precisely at 121.6 nm), such that the Hydrogen Lyman-α line light can be effectively transmitted within the interferometer without the need to work in entirely in a high vacuum environment. This enhanced ability to transmit this light within the interferometer 300 without a high-vacuum light path significantly enhances the performance of the interferometer by comparison with conventional interferometers that employ visible or near-ultraviolet light. As will be described below, in the present embodiment, the transmission of the Hydrogen Lyman-α light particularly occurs through a $N_2$ environment but, as already discussed above, the advantages of using the Hydrogen Lyman-α light particularly in terms of low absorption remain substantially true even in such an environment.

As shown in FIG. 12, the interferometer 300 more particularly includes a hermetically-sealed housing or hermetic enclosure 310 having an inner region 349 that is Nitrogen purged through a gas path 350. Within the hermetic enclosure 310 (within the inner region 349) are positioned and supported a condenser lens 311, a beam splitter 312, an objective (or focusing) lens 313, a reference mirror 314 and a tube lens 315. Additionally, inside the enclosure 310, there is negligible absorption of Hydrogen Lyman-α light that is transmitted therewithin notwithstanding the Nitrogen gas within the enclosure. Further as shown, in the present embodiment a Hydrogen Lyman-α light source 320 is attached to the enclosure 310 along a first side 321 thereof, and a camera system (or imaging detector) 330 is attached to the enclosure 310 along a second side 322 thereof. The camera system 330 in the present embodiment includes both a Hydrogen Lyman-α light converter 331 and a camera device 332. The objective lens 313 is positioned internally along a third side 323 of the enclosure 310 proximate a window 360 in that third side, where the third side in the present embodiment is on the opposite side of the enclosure 310 relative to the first side 321 (and the second side 322 extends between the first and third sides). The window 360 is a transparent window that separates the ambient atmosphere (air) outside of the enclosure 310 from the enclosure (or the inner region 349 of the enclosure).

Depending upon the embodiment, a variety of different specific components can serve as the components of interferometers such as the interferometer 300 of FIG. 12 that are encompassed herein. In the present embodiment, the interferometer 300 of FIG. 12, can employ, as the Hydrogen Lyman-α light source 320, a light source having a plasma diameter of approximately 2.5 mm and providing a flux of approximately $10^{14}$ Hydrogen Lyman-α photons/sec/sr over 28° full angle, as is available from Resonance Ltd. of Barrie, Ontario, Canada. Alternatively, other Hydrogen Lyman-α light sources can be employed in the interferometer 300 including, for example, the light source 10 discussed above with respect to FIG. 9. As for the beam splitter 312, in the present embodiment the beam splitter is a commercially available product from Acton Optics and Coatings of Acton, Mass., which is designed for the Hydrogen Lyman-α wavelength range, and can be a beam splitter having a reflectance (R) of approximately 0.35 and a transmission (T) of approximately 0.2. Also, each of the condenser lens 311 and the tube lens 315 can be made from LiF or $MgF_2$, be 1.5 mm thick, and have a radius of curvature (R) equaling 20 mm convex plano.

With respect to the reference mirror 314, it is located proximate to a fourth side 324 of the enclosure 310 that is opposite the second side 322 (and extends between the first and third sides 321 and 323). In the present embodiment, the reference mirror 314 is fixedly attached/arranged in relation to the enclosure 310. However, in other embodiments, the reference mirror 314 can be configured with a piezoelectric (PZT) transducer, so that phase-shifting interferometry can be performed. Under average conditions for visible phase-shifting interferometry, λ/50 resolution in feature height can be obtained. Under ideal conditions, λ/2000 resolution can be obtained. If only λ/50 resolution is obtained with the Hydrogen Lyman-α light source 320, around 2.4 nm feature height resolution can be measured, and λ/2000 performance would resolve 0.06 nm feature heights. It should be also noted that, in the present embodiment, the reference mirror 314 is an Al coated mirror with a $MgF_2$ enhancement layer. These simple coatings provide over 80% reflectivity at the Hydrogen Lyman-α wavelength of 121.6 nm.

Figure 13:
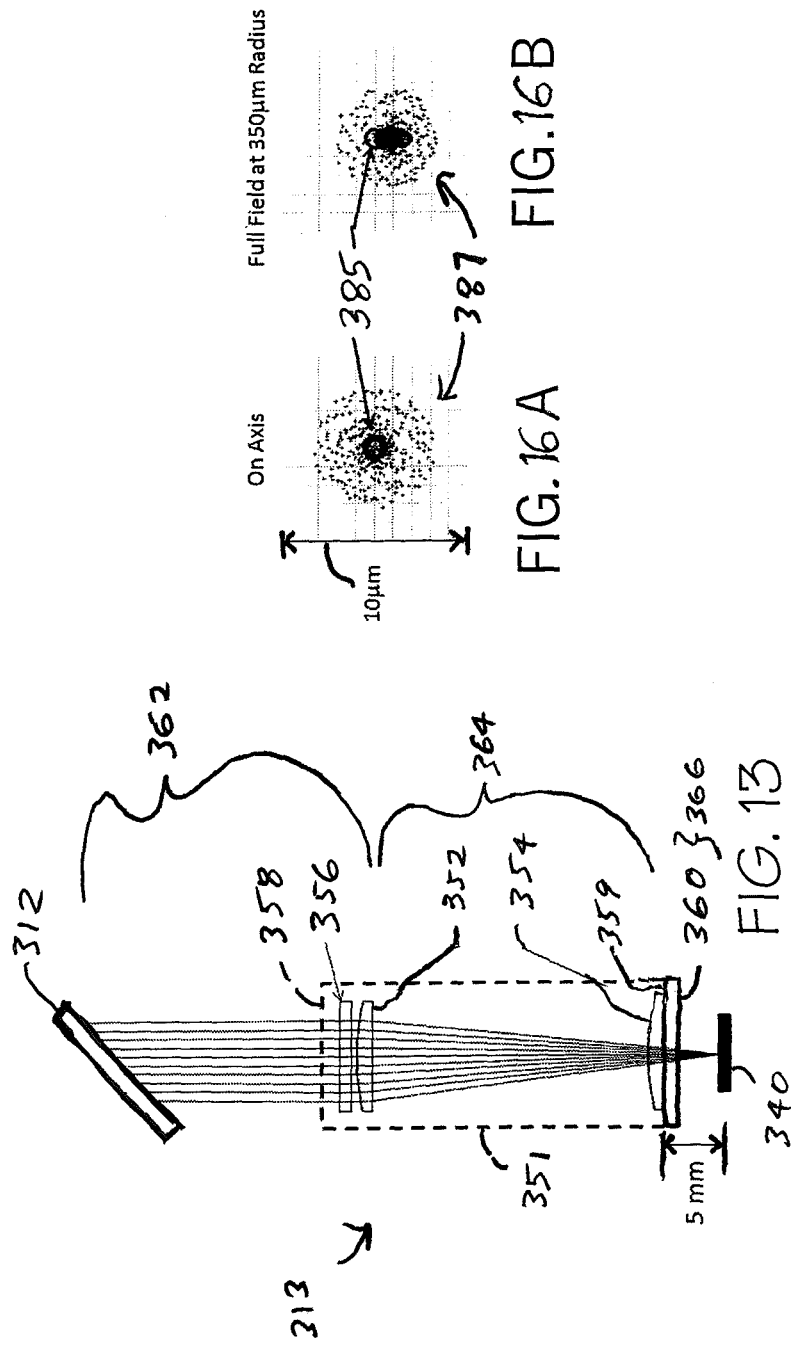
FIG. 13 shows in further detail an objective lens employed in the interferometer of FIG. 12, in accordance with one embodiment of the present invention.

As for the objective (or focusing) lens 313 of the interferometer 300, this component has significance particularly when magnification of a small area of the surface of the sample 340 is desired. Again, depending upon the embodiment the objective lens 313 can take a variety of forms, albeit it should be appreciated that custom high-performance optics can be fabricated but that the components are often expensive. Further in regard to the objective lens 313, FIG. 13 shows several features of the present embodiment of the objective lens 313 in more detail. As shown, the objective lens 313 particularly includes an objective lens mounting tube 351 within which are positioned first and second refractive lenses 352 and 354, respectively, and a phase plate or "aspheric diffractive corrector" (or simply aspheric corrector) 356. The phase plate 356 is positioned proximate a first end surface 358 of the objective lens mounting tube 351, at which light passing transmitted through the beam splitter 312 enters the mounting tube, and the first refractive lens 352 is positioned proximate to, but farther inwardly from the first end surface 358 than, the phase plate. By comparison, the second refractive lens 354 is positioned adjacent to a second end surface 359 of the objective lens mounting tube 351 along which is positioned the window 360, and through which light being communicated to and from the sample 340 passes.

Each of the first and second refractive lenses 352 and 354 in the present embodiment is made from LiF, is convex plano in shape, is 10 mm in diameter, is 1.5 mm thick, and has a radius of curvature (R) equaling 20 mm (as was the case with the condenser lens 311 and the tube lens 315). $MgF_2$ can also be used as a lens material with possibly a different radius of curvature. As for the phase plate (or aspheric diffractive corrector) 356, in the present embodiment the phase plate is made from LiF or $MgF_2$ and can be fabricated (directly written) with gray-scale photoresist processing. More particularly, in the present embodiment, the phase plate 356 can be a laser-written gray scale photolithography and direct ion-beam pattern transfer using a neutral Ar beam. That is, the fabrication process involves using a grayscale laser writer, to expose a low-contrast polyimide photoresist and form a topographical pattern in the photoresist after development. The photoresist pattern is then transferred into the substrate, which in this example is LiF, using ion milling. The phase plate can be designed (as can the rest of the optical system) through the use of Zemax® lens (optical) design software mentioned above.

Figure 14:
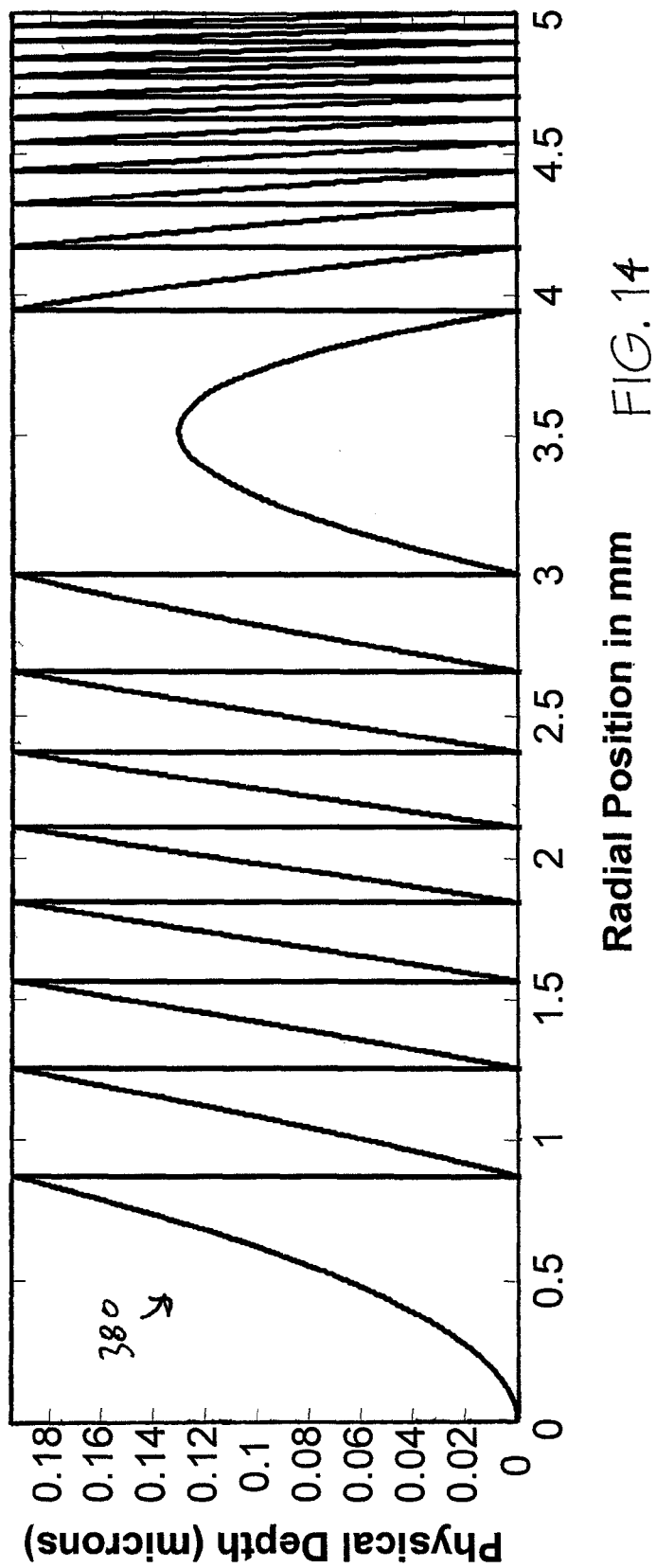
FIG. 14 is a graph showing an example LiF surface profile for a phase plate (aspheric diffractive corrector) utilized in the objective lens of FIG. 13.

FIG. 14 provides a graph 380 showing an example LiF surface profile for the phase plate (aspheric diffractive corrector) 356 in the present embodiment. The horizontal axis of the graph 380 is the radius of the phase plate 356 with a maximum radius of 5 mm. The vertical axis of the graph 380 is the depth of the pattern transferred into the LiF. The maximum depth is defined by one wavelength of optical path difference (OPD) through the part, which is 195 nm. The minimum feature size is about 60 μm, which is well within the operating range of maskless grayscale writers. Although the profile is diffractive in nature, the narrow bandwidth of the Hydrogen Lyman-α source precludes any diffractive issues, such that the phase plate 356 can indeed operate as a simple phase corrector plate. Notwithstanding the particular example feature shown in FIG. 15, it should be understood that, in other embodiments, the phase plate can have other features and/or be fabricated in different manners.

Additionally as illustrated in FIG. 13, light transmitted through the beam splitter 312 proceeds in a collimated fashion within a first region 362 extending from the beam splitter 312 through the first end surface 358 and the phase plate 356 and up to the first refractive lens 352. The first refractive lens 352 then serves to focus the light within a second region 364 extending between the first refractive lens 352 and the second refractive lens 354, and the second refractive lens 354 then further serves to focus the light so as to proceed within a third region 366 extending between the second end surface 359 (the plano surface of the second refractive lens 354) through the window 360 to a region of interest on the sample 340. In the present example, the third region 366 is 5 mm in distance, although this can vary depending upon the embodiment. It should be appreciated that, in the present embodiment, the objective lens 313 is nearly diffraction limited with numerical aperture (NA) equaling 0.15. Additionally, it should also be appreciated that light reflected off of the sample 340 follows a path that is essentially the reverse of that described above in regard to FIG. 13, such that the light is again collimated or substantially collimated as it returns to the beam splitter 312 by way of the first region 362.

Also, in the present embodiment as shown in FIG. 12, the camera system 330 can employ a conventional camera device such as a CCD device as the camera device 332 for storing images (e.g., storing images electronically). Additionally, the camera system 330 can also include, as the Hydrogen Lyman-α light converter 331, a microchannel plate (MCP) detector (which can also be referred to as an image detector or an image intensifier), which receives light arriving from the beam splitter 312 as is focused onto the MCP detector by the tube lens 315. In the present embodiment, the Hydrogen Lyman-α light converter 331 (MCP detector) is solar blind and has a quantum efficiency (QE) of approximately 0.4, a channel diameter equaling 10 μm, and an 18 mm effective diameter, such as is available from Del Mar Photonics, Inc. of San Diego, Calif. The MCP detector serving as the converter 331 is a slight modification from units manufactured to operate in high vacuum, where the MCP unit is sealed with a thin $MgF_2$ window. Because the MCP detector serving as the converter 331 is solar blind, it will not detect the Balmer lines or any near ultraviolet or visible radiation, and shorter wavelengths will be effectively filtered by the LiF and the beam splitter. A photon budget, including considerations for the source flux, material transmission and Fresnel reflections from surfaces indicates that the number of photons incident on the MCP detector (serving as the converter 331) is over 500 per frame per channel at a 10 frame/sec readout rate and 1% sample reflectivity. In the present example embodiment, the image on the MCP detector (image intensifier) is magnified by 20 times, although in other embodiments a different amount of magnification is provided.

As for the sample 340, this again is intended to be representative of any of a variety of samples or targets of interest depending upon the embodiment. For example, in the present embodiment, the sample 340 can be a laser-written photoresist and lift-off process binary structures with metallic patterns on various substrates. (Also, in at least one sample 340 that can be used as a test sample, the sample can be an Al coated mirror with a $MgF_2$ enhancement layer. As with the reference mirror 314, these simple coatings can provide over 80% reflectivity at the Hydrogen Lyman-α wavelength of 121.6 nm.) In regard to the sample 340, it should be appreciated that various sample materials of interest can have a variety of degrees of reflectivity (or reflectance) and in particular can have much higher reflectivity than the 1% reflectivity mentioned above, in which case the signal-to-noise ratio of the detection process should be much greater than the square root of 500, that is, much greater than about 22 (mechanically, adjustments will be designed to operate through the hermetic enclosure). Indeed in order to construct a Hydrogen Lyman-α interferometer such as the interferometer 300, contrast of the sample 340 must be understood in terms of the expected reflectance at the source wavelength. Table 3 lists typical materials, their associated complex refractive indices (n+ik) and the expected reflectivities (reflectances) at normal incidence. The different materials show differences in reflectivity large enough to justify the goal of sufficient image contrast with the Hydrogen Lyman-α interferometer. Relatedly it should be appreciated that, due to its low absorption and high refractive index, LiF is a preferred lens material for the interferometer 300.

TABLE 3

OPTICAL CONSTANTS FOR EXAMPLE MATERIALS
AT THE HYDROGEN LYMAN ALPHA LINE (121.6 NM)

| Material | n + ik | Reflectance ($\theta_i = 0°$) |
| --- | --- | --- |
| Polysilicon | 1.6403 + i 3.4374 | 65.08% |
| Silicon | 0.2972 + i 1.3320 | 65.61% |
| Silicon (amorphous) | 0.4444 + i 1.0993 | 46.05% |
| Copper | 1.0464 + i 0.8044 | 13.43% |
| Silicon Nitride (noncrystalline) | 1.9296 + i 1.5063 | 28.87% |
| SiO2 (glass) | 2.2471 + i 0.6954 | 18.49% |
| Magnesium Fluoride | 1.6138 + i 8.0E−5 | 5.51% |
| LiF | 1.6235 + i 8.04303E−6 | 5.65% |
| Chromium | 0.9933 + i 0.7233 | 11.64% |
| Molybdenum | 0.812 + i 0.930 | 21.70% |
| Aluminum | 0.04464 + i 1.1134 | 92.34% |

It should be appreciated from FIG. 12 that the interferometer 300 operates by communicating the Hydrogen Lyman-α light along two different light paths. A first "reference" light path is one in which first light emitted from the Hydrogen Lyman-α light source 320 proceeds up to the beam splitter 312 via the condenser lens 311 in a direction generally indicated by a first arrow 370, then is reflected off of the beam splitter so as to proceed in a direction generally indicated by a second arrow 372 to the reference mirror 314, then is reflected off of the reference mirror back to the beam splitter (thus proceeding in a direction that is the reverse of that indicated by the second arrow 372), and then passes through the beam splitter and is transmitted along a direction generally indicated by a third arrow 374 via the tube lens 315 to the camera system 330. By comparison, a second "test" light path is one in which second (additional) light emitted from the Hydrogen Lyman-α light source 320 proceeds up to the beam splitter 312 via the condenser lens 311 in a direction generally indicated by a first arrow 370, then is transmitted through the beam splitter so as to continue to proceed to, through, and out the objective lens 313 so as to arrive at the sample 340 along a direction generally indicated by a fourth arrow 376, then (at least partly) is reflected off of the sample so as to proceed back to, through, and out of the objective lens 313 and to the beam splitter (thus proceeding in a direction that is the reverse of that indicated by the fourth arrow 376), and then finally is reflected off of the beam splitter so as to again be transmitted along the direction generally indicated by the third arrow 374 via the tube lens 315 to the camera system 330. In the present embodiment, the long conjugate to the image plane (at which the camera system 330 and particularly the Hydrogen Lyman-α light converter 331 are situated) is 495 mm from the limiting aperture of the system.

Figure 15:
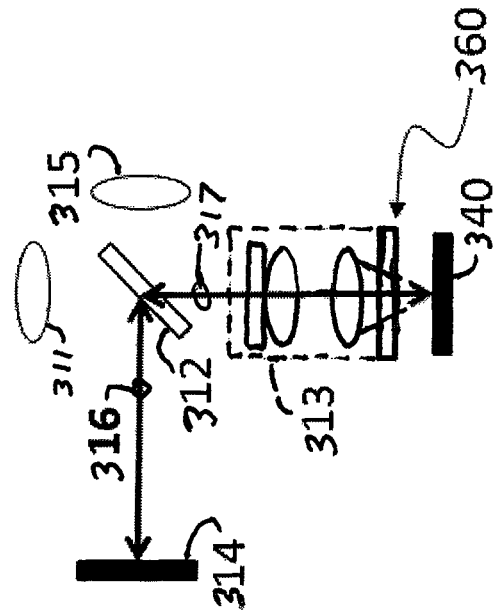
FIG. 15 is an additional schematic showing portions of the interferometer of FIG. 12 and particularly illustrating two different optical path lengths associated respectively with a reference arm and a test arm of the interferometer.

Given these two light paths, it will be appreciated that the two light paths are identical in length in terms of the distances associated with the first arrow 370 (that is, the distance between the light source 320 and the beam splitter 312) and with the third arrow 374 (that is, the distance between the beam splitter 312 and the camera system 330. However, it will also be appreciated the two paths differ because, in the first light path, light passes back and forth between the beam splitter 312 and the reference mirror 314 but, in the second light path, light passes back and forth between the beam splitter 312 and the sample 340. Referring additionally to FIG. 15, which is a schematic diagram highlighting certain portions of the interferometer 300 shown in FIG. 12, these respective portions of the first and second light paths are shown as a first optical path length 316 constituting a reference arm and a second optical path length 317 constituting a test arm. In the present embodiment, the difference of these first and second optical path lengths 316 and 317, which are shown here as a double-pass configuration, should be less than the coherence length of the interferometer. Further, the coherence length of the spectral doublet forming the Hydrogen Lyman-α light is approximately $\lambda^2/\Delta\lambda \approx 150$ mm, so coherent effects can be expected in some instrument configurations. The line width of a reasonably high-power Hydrogen Lyman-α light source is presently 0.004 nm, which allows for nearly 3.7 mm of path length difference between arms of the interferometer (that is, assuming that the Hydrogen Lyman-α light source 320 has a bandwidth of 0.004 nm, the path difference cannot be greater than about 3.7 mm). This path length difference is relatively very large and would not necessitate any special considerations when constructing the instrument, beyond normal machining tolerances.

In view of the above description, it should be understood that the interferometer 300 can particularly be employed to detect surface topography and surface aberrations of the sample 340, in the form of image information regarding such surface topography/aberrations that is received and collected by the camera system 330 and particularly the camera device 332. The image information received and collected by the camera system 330 particularly is indicative of interference between (a) the first light that has traversed the first light path described above and particularly doubly traversed the first optical path length 316 and (b) the second light that has traversed the second light path described above and particularly doubly traversed the second optical path length 317. Such interference will typically occur insofar as the first and second optical path lengths 316 and 317 (and correspondingly the first and second light paths described above) typically differ from one another because of the variations in surface topography/surface aberrations of the sample 340.

Upon the image information being received by the camera device 332, the image information can then be stored in one or more memory devices, processed at one or more computer devices, and/or transmitted or communicated via one or more communications links to other devices or locations (not shown). Indeed, as discussed above with respect to the camera module 90 of FIG. 1, depending upon the embodiment, the camera system 330 and particularly the camera device 332 is capable of a variety of imaging operations, image processing operations and other operations after receiving and sensing/detecting. In some embodiments, the camera device 332 records imaging information on film that is then processed externally by a third party, or more immediately by the camera device itself. In other embodiments, the camera device 332 stores imaging information on memory within or associated with the camera module. This imaging information can, in at least some embodiments, be stored digitally. Further, in some embodiments, the camera device 332 is capable of performing various digital processing operations upon the imaging information, as well as capable of transmitting the processed (or unprocessed) imaging information to other devices (e.g., computer systems) associated with or remote from the camera module. Such transmission can occur, in at least some embodiments, by various network communication links or even via the internet or the World Wide Web, via hardwired or wireless communication links. In some embodiments, the camera module itself is capable of displaying (e.g., on a video screen or monitor) the images, and/or capable of printing hardcopies of images.

With respect to actual image information collected by the camera device 332, FIGS. 16A and 16B are geometrical spot diagrams additionally provided to show example optical aberrations as were calculated using the Zemax® optical design software mentioned above, as properly adjusted for working at the Hydrogen Lyman-α light wavelength. FIG. 16A shows the image information determined on axis, and FIG. 16B shows the image information at full field at 350 µm radius. As a consequence of residual aberrations, the geometrical spot diagrams of FIGS. 16A and 16B indicate that most of the energy is contained within the diameter of a diffraction-limited Airy spot 385 having a diameter of 0.98 µm, but a small background pedestal 387 is present with diameter about three times the Airy disk diameter. These spot diagrams are similar to the expected images of points on the sample, and are referred to the dimensions of the sample. At the camera device 332, the distributions are the same shape but 20× larger. Note that the designed Airy spot diameter at the MCP image intensifier is about twice the radius of one MCP channel. Therefore, detector sampling is sufficiently fine. Additionally, the 700 µm field at the sample is magnified by 20× to the image intensifier for a field diameter of about 14 mm, which fits well into the 18 mm effective diameter of the MCP. The number of Airy resolution elements across the field at the MCP is about 777, with the number of aberrated elements two or three times fewer, depending on the types of features on the sample. This pixel format fits well with several commercially available low-noise CCD cameras as can serve as the camera device 332. Such a CCD camera reimages the phosphor screen of the MCP in order to minimize cost. In alternative designs, fiber-light-pipe(s) can be employed to direct coupling.

Although the above description of the interferometer 300 emphasizes the generation, transmission, and receipt/use of Hydrogen Lyman-α light, it should be appreciated that in at least some embodiments the light source 320 is a multiple-wavelength light source that not only generates light at the Hydrogen Lyman-α line but also generates additional light at one or more other wavelengths or wavelength ranges such as visible, infrared, ultraviolet, or near-ultraviolet wavelengths, and that in at least some such embodiments the interferometer then transmits and receives/uses that additional light (or at least a narrow portion of that light within a second wavelength range). In some such embodiments, it is actually a single device serving as the light source 320 that can generate both the Hydrogen Lyman-α light and the other light (e.g., at the visible, infrared, ultraviolet, or near-ultraviolet wavelengths), and in other such embodiments actually multiple light generating devices are present that can all be encompassed generally within the light source, even though one of those devices specifically is for generating the Hydrogen Lyman-α light and other(s) of those devices is or are for generating the other light.

Such additional light at one or more other wavelengths or wavelength ranges such as visible, infrared, ultraviolet, or near-ultraviolet wavelengths can be used during operation of the interferometer 300 for various purposes including, for example, alignment purposes. Further for example, the additional light can be blue light or green light respectively emitted by a blue laser diode or green laser diode (or blue light emitting diode or green light emitting diode), respectively, at around 408 nm or 540 nm, respectively. In such embodiments, the camera system 330 particularly is designed to accommodate both Hydrogen Lyman-α light and the additional light at the one or more other wavelengths or wavelength ranges and, in some embodiments, includes two different camera devices or light detectors for the two different types of light. Indeed, similar to as was discussed above in regard to the optical microscope 100, in at least some embodiments the interferometer is operated in a manner in which first, before the providing of any light from the light source 320 at the Hydrogen Lyman-α line, an operator will locate, align, or position a feature or structure of interest (e.g., the sample 340 or a portion thereof) using a visible light source (e.g., 400 nm<λ<700 nm), which is not shown in FIG. 12. Upon locating the feature of interest, the operator then switches on the light source 320 (and switches off the visible light source). At that point, the Hydrogen Lyman-α light is directed from the light source 320 to the sample 340 (as well as to the mirror 314), which in turn results in the providing of at least some of that light to the camera system 330, at which point that image information can again be processed, stored, viewed, or transmitted, or otherwise used in a variety of manners as already discussed above in relation to the camera module 90 and otherwise above.

It should additionally be appreciated that at least some interferometer embodiments encompassed herein are advantageous in that there is a split optical path for the reference beam, such that the majority of the optical path of the Hydrogen Lyman-α light is in a Nitrogen (N$_2$) nonabsorbent (or substantially nonabsorbent) atmosphere, but the test object (i.e., the sample 340) is in the ambient (air) atmosphere, with no requirement for vacuum or special handling. Such an interferometer can have a vertical resolution of λ/1000=0.12 nm, based on current art for direct-phase-measurement interferometers. This height resolution is five times smaller than interferometers using visible wavelengths. The sample can be in a non-vacuum dry environment and requires no special preparation. The interferometer can be configured to test relatively large (e.g., 1" diameter class) surfaces in a standard Michelson geometry, or it can be used in a microscope. One example configuration in this regard is a Mirau microscope, which would directly provide both reference and test beams for the interferometer. Further, in at least some interferometer embodiments encompassed herein, additional light at a second wavelength (or multiple second wavelengths) in addition to light at the Hydrogen Lyman-α line is employed. The additional light at the second wavelength (or multiple second wavelengths) can be used for alignment through the optical system, and the Hydrogen Lyman-α light can be used for interferometric sensing/imaging.

Figure 17:
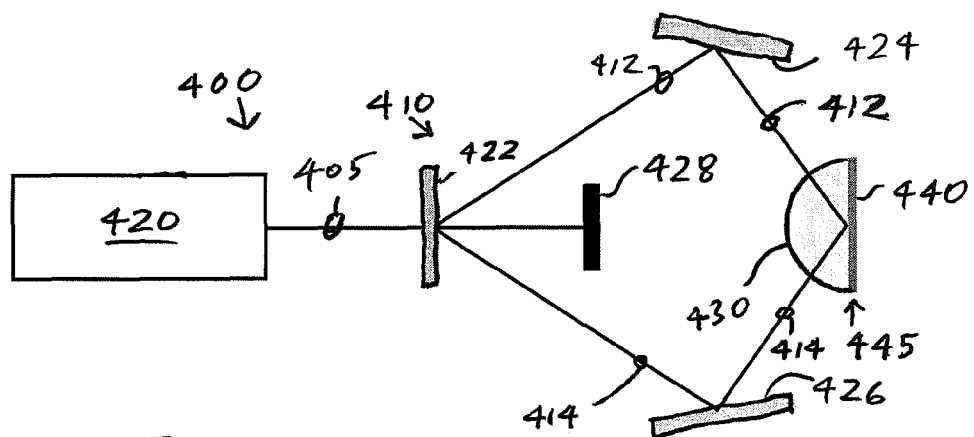
FIGS. 17 and 18 are additional schematic diagrams showing first and second interferometric lithography systems in accordance with two example embodiments.
Figure 18:
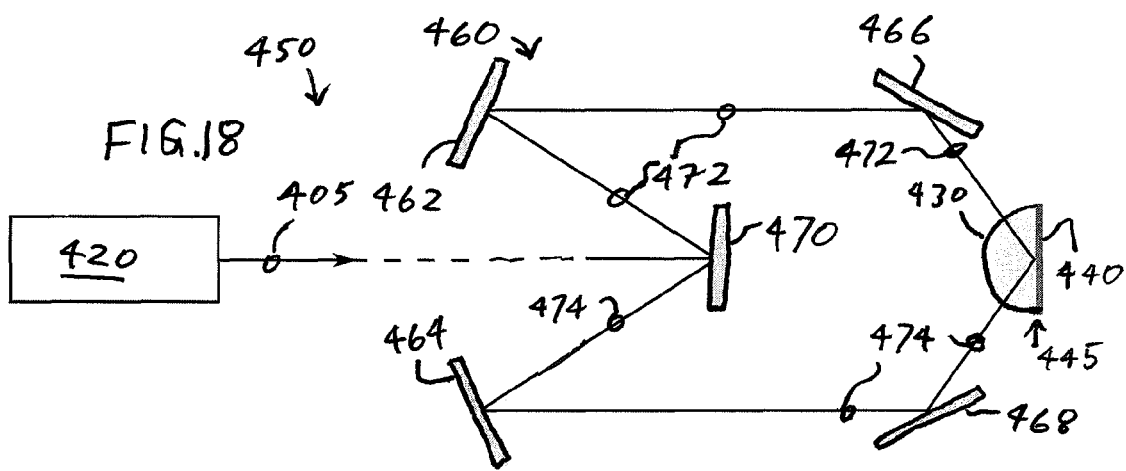

Turning now to FIGS. 17 and 18, in addition to the above discussion concerning interferometers such as the interferometer 300, the present invention is also intended to encompass additional systems for performing lithography that employ interference techniques, that is, interferometric lithography systems. More particularly, FIGS. 17 and 18 respectively show a first interferometric lithography system 400 and a second interferometric lithography system 450, respectively, each of which can also be considered to be an immersion lithography system or interferometric exposure tool, operating in transmission mode. As shown, each of the first and second interferometric lithography systems 400 and 450 operates using Hydrogen Lyman-α light (at 121.6 nm) generated by a spatially coherent Hydrogen Lyman-α light source 420. Also, each of the first and second interferometric lithography systems 400 and 450 includes a respective two-beam interference setup 410 and 460, respectively, by which light proceeding along two different paths is directed to a high-index solid immersion lens (SIL) 430 that is positioned immediately in front of a target 440 such as a wafer represented positioned along a wafer plane 445. Although the two-beam interference setups 410 and 460 differ from one another, in the present embodiments the SILs 430, targets 440, and wafer planes 445 provided in each of the first and second interferometric lithography systems 400 and 450 are the same. Also, although the SIL 430 can take various forms depending upon the embodiment, in the present embodiment the SIL in each of the first and second interferometric lithography systems 400 and 450 is made of LiF.

More particularly with respect to the two-beam interference setup 410 providing the two light paths in the first interferometric lithography system 400, FIG. 17 particularly shows that setup as including a transmissive mask 422, first and second mirrors 424 and 426, respectively, and a zeroth order block 428, in addition to the SIL 430 and target 440 along the wafer plane 445. As illustrated, Hydrogen Lyman-α light 405 emitted from the Hydrogen Lyman-α light source 420 is directed to the transmissive mask 422, which serves to divide the light into a +1$^{st}$ order component 412 and a -1$^{st}$ order component 414. The +1$^{st}$ order component 412 in turn proceeds from the transmissive mask 422 to the first mirror 424, at which that component is then reflected so as to proceed to the SIL 430, which then finally directs that light component to the target 440. By contrast, the -1$^{st}$ order component 414 proceeds from the transmissive mask 422 to the second mirror 426, at which that component is then reflected so as to proceed to the SIL 430, which then finally directs that light component to the target.

As for the two-beam interference setup 460 providing the two light paths in the second interferometric lithography system 450, FIG. 18 particularly shows that system as including a reflective mask 470 and first, second, third, and fourth mirrors 462, 464, 466, and 468, respectively, in addition to the SIL 430 and target 440 along the wafer plane 445. As illustrated, the Hydrogen Lyman-α light 405 emitted from the Hydrogen Lyman-α light source 420, which can be considered zeroth-order light, is directed to the reflective mask 470, which serves to divide the light into a +1$^{st}$ order component 472 and a -1$^{st}$ order component 474. The +1$^{st}$ order component 472 in turn proceeds from the reflective mask 470 to the first mirror 462, at which that component is then reflected so as to proceed to the third mirror 466, which in turn directs that component to the SIL 430, which then finally directs that light component to the target 440. By contrast, the -1$^{st}$ order component 414 proceeds from the reflective mask 470 to the second mirror 464, at which that component is then reflected so as to proceed to the fourth mirror 468, which in turn directs that component to the SIL 430, which then finally directs that light component to the target 440.

Thus, in each of the first and second interferometric lithography systems 400 and 450, the initial beam of light 405 from the light source 420 is divided into two parts but then each part is directed through the SIL 430 and recombined interferometrically to produce a standing-wave pattern (which in the present example embodiment is a 15 nm standing-wave pattern). Depending upon the embodiment, various resist materials and processes can be cost-effectively developed and utilized at the wafer plane 445. With respect to the interference more particularly, the interference of two plane-waves of wavelength λ with an interbeam angle α gives rise to interference fringes of half-period or half-pitch p/2, given by $$(p/2) = \frac{\lambda}{4n \sin(\alpha/2)} \quad (1)$$

where n is the refractive index of the medium. The quantity n sin(α/2) is known as the numerical aperture (NA). The half-pitch (p/2) is a measure of resolution, and also is referred to as the critical dimension (CD) in lithographic patterning, as it can represent a tangible feature (line or space).

By virtue of such operation, each of the first and second interferometric lithography systems 400 and 450 can serve as a direct line width patterning tool that is well beyond state of the art of conventional lithography systems operating at 13 nm or 193 nm. In particular, with a significant shrink in wavelength to the Hydrogen Lyman-α line and increase in NA (e.g., to NA's above values accomplishable in air, such as NA>1.0), a tremendous improvement in resolution is possible by comparison with many conventional lithography systems. That is, the use of two-beam interference can provide infinite depth of focus, and the use of a solid immersion lens such as the SIL 430 provides the potential for high values of numerical aperture (NA) or even hyper-NA's (NA>1.0). Given that resolution (R) equals $k_1$ (λ/NA), and assuming that the numerical aperture (NA) is pushed to extremes in at least two of its components, and it is expected that interferometric lithographic systems employing Hydrogen Lyman-α light such as the first and second interferometric lithography systems 400 and 450 can produce images in world-record half-pitch regime. More particularly in this regard, FIGS. 19A-

19C show data illustrating example predicted performance of the Hydrogen Lyman-α light source 420 in interferometric configuration corresponding to either of the first and second interferometric lithography systems 400 and 450, where the results assume 50% duty cycle for CD. FIG. 19A particularly is a graph illustrating predicted CD as a function of NA (where $\theta=\alpha/2$), for two beam interference using Hydrogen Lyman-α (121.6 nm) light depending upon air versus LiF SIL transmission. FIGS. 19B and 19C show predicted spatial variation patterns (e.g., patterns that would occur at the target 440). In regard to these results, it should be appreciated that other pitch doubling and CD-shrinking techniques (e.g., some other techniques already in use today) could possibly be employed with greater success than with an ArF, which has a 58.7% longer wavelength.

Although not shown in FIGS. 17-18, it should also be appreciated again in relation to at least some embodiments of the interferometric lithography systems encompassed herein, as is the case with at least some of the embodiments of optical microscopy and interferometric systems discussed above, the light source 420 is a multiple-wavelength light source that not only generates light at the Hydrogen Lyman-α line but also generates additional light at one or more other wavelengths or wavelength ranges such as visible, infrared, ultraviolet, or near-ultraviolet wavelengths. In such embodiments, the additional light at one or more other wavelengths or wavelength ranges such as visible, infrared, ultraviolet, or near-ultraviolet wavelengths can be used during operation of the interferometric lithography systems for various purposes including, for example, alignment purposes. And in at least some such embodiments, the interferometric lithography systems are operated in a manner in which first, before the providing of any light from the light source 420 at the Hydrogen Lyman-α line, an operator will locate, align, or position a feature or structure of interest (e.g., the target 440 or a portion thereof) using a visible light source (e.g., 400 nm<λ<700 nm), which is not shown in FIGS. 17-18. Upon locating the feature of interest, the operator then switches on the light source 420 (and switches off the visible light source). At that point, the Hydrogen Lyman-α light is directed from the light source 420 to the target 440.

Additionally, although the lithography systems 400 and 450 shown in FIGS. 17 and 18 each include the SIL 430, it should also be understood that, in alternate embodiments, the same or substantially similar systems can be implemented without the SIL 430 (that is, without any SIL), for production of patterns with slightly lower resolution (in some such embodiments, the SIL is not present and rather only air is present where the SIL would otherwise be). Further, although a SIL such as the SIL 430 can be employed in some embodiments to separate an $N_2$ atmosphere lithography system (e.g., an interior region of the lithography system) from a target such as the target 440, which can be in air, in some other embodiments a simple LiF or $MgF_2$ window can replace the SIL 430 for a lower resolution system. In addition, in some other alternate embodiments, the SIL 430 can be replaced with a solid immersion prism, with the target 440 being in air. Indeed, the present disclosure is intended to encompass numerous different lithography systems that have SILs, do not have SILs, and/or have other types of lenses, windows, prisms (with or without immersion fluids), or other optical structures or features in place of SILs. Also, the materials or media used for the SILs and shapes of the SILs in lithography systems employing SILs can vary depending upon the embodiment.

From the discussion provided above, it should be evident that embodiments of the present invention, by utilizing light at (or near) the Hydrogen Lyman-α line, are capable of allowing high-resolution optical microscopy, interferometry, and interferometric lithography, without the need for a high vacuum light path between the light source, the camera and the target. The present invention is intended to encompass a wide variety of structures, components, and methods of operation (and construction) of optical microscopes, interferometers, and interferometric lithography systems capable of operating at (or near) the Hydrogen Lyman-α line that differ from the particular embodiments described above, which are merely intended to be exemplary. For example, while the above embodiments particularly envision the use of Hydrogen gas, Deuterium is equally applicable in at least some embodiment of the present invention. Also for example, while in the embodiment of FIG. 1 the objective lens 80 both communicates light to the target 85 and communicates reflected light away from the target 85, in alternate embodiments two different lens devices (or other devices) could be employed to perform these two operations. Similarly, in the embodiment of FIG. 12, the objective lens 313 can be replaced with other lens designs or combinations of lenses.

It should be appreciated that the present invention is intended to encompass numerous other embodiments in addition to, and variations of, the embodiments disclosed herein. In at least some such other embodiments, one or more of the subcomponents described in one or more of the systems described above are modified. For example, depending upon the embodiment, the lenses (e.g., the objective lenses 80 and 313) or other optical components used in any of the optical microscopy, interferometry, and interferometric lithography systems discussed above can be modified. Further for example, in some such embodiments, the lens designs are particularly suited for operation of the system in two wavelength ranges, namely, in the Hydrogen Lyman-α wavelength range and in an additional wavelength range such as one or more of (or one or more portions of) the visible, infrared or ultraviolet wavelength ranges.

Further in this regard, FIGS. 20A and 20B show two examples of alternate embodiments of lenses 500 and 550 that can be utilized in alternate embodiments of the optical microscopy, interferometric, interferometric lithography, and other systems encompassed herein, for example, in place of the objective lenses 80 or 313 discussed above. The lens 500 of FIG. 20A particularly is a 0.8 NA design covering a +/−75 μm field. The Airy spot radius for the lens 500 is 92 nm, which would produce a useable resolution of between 45 nm and 55 nm (depending on how resolution is defined). As shown, the lens 500 includes a primary (concave) mirror 502, a secondary (convex) mirror 504, and a front diverger 506 within a housing 508 (shown partly in cutaway) that defines an interior vacuum/inert gas region 510 within which a high vacuum is maintained or within which inert gas is provided. The secondary mirror 504 more particularly is a spherical mirror, and also the front diverger 506 is a refractive aspheric diverger that is used near the vertex of the aspheric primary mirror. Additionally, the housing 508 includes a field corrector/separator 512 that forms a transmission window through which Hydrogen Lyman-α light can pass between the region 510 and an external region 514 outside of the housing 508 that is at other than high vacuum and that can be air at atmospheric pressure. Thus, the field corrector/separator 512 of the lens 500 serves a purpose as the "separator" of the interior vacuum/inert gas region 510 and the external ("other than high vacuum") region 514.

The lens 500 is positioned in relation to an object plane 516 also shown in FIG. 20A, at which a target can be positioned. As shown, the object plane 516 is located within the external region 514, at a distance 518 from the field corrector/separator 512 that constitutes a space (or separation) through which the Hydrogen Lyman-α light will pass through the air at atmospheric pressure. In the present example embodiment, the distance 518 can be 1 cm. In the present embodiment, the lens 500 is catadioptric using LiF refractive components. Also in the present embodiment, the lens system employing the lens 500 is designed to use a HeNe laser at 632.8 nm (red color) for alignment, thereby making the system manufacturable. As illustrated, Hydrogen Lyman-α light 530 reaching and reflected off the target at the object plane 516 proceeds through the distance 518 and through the field corrector/separator 512 to the primary mirror 502, which reflects that light to the secondary mirror 504 and out of the lens 500 by way of the front diverger 506, with obscuration occurring at a location 520 past the front diverger (that is, not within the region between the front diverger and the secondary mirror). It will be appreciated that Hydrogen Lyman-α light can proceed in substantially the opposite manners already discussed when light enters the lens 500 and is directed to the target at the object plane 516.

By comparison with FIG. 20A, FIG. 20B shows the lens 550 to include several components that are similar or identical to those of the lens 500. In particular, the lens 550 includes a primary mirror 552, secondary mirror 554, and front diverger 556 that can be identical to, or substantially similar to, the primary mirror 502, secondary mirror 504, and front diverger 506 of the lens 500, with obscuration again occurring at a location 570 on the side of the front diverger opposite the side of the front diverger that is facing the secondary mirror. In the embodiment shown, the lens 550 also includes a field corrector 562, and an object plane 566 at which a target can be positioned is located a distance 568 from the field corrector. In the present embodiment, there is no housing that contains the primary mirror, secondary mirror, or front diverger that would correspond to the housing 508 of FIG. 20A, and there is no separation between vacuum/inert gas regions and atmospheric air regions, but rather the lens 550 is entirely within air at atmospheric pressure (albeit in an alternate embodiment such a housing could again be present). However, in contrast to the lens 500, the lens 550 additionally includes a solid immersion lens (SIL) 572 positioned along the object plane 566, in air at atmospheric pressure, between the object plane and the field corrector 562. FIG. 20C provides an additional detail view showing the SIL 572 along the object plane 566. In the present embodiment, the SIL is designed to exhibit a numerical aperture (NA) equaling 1.25, and to have an Airy spot radius of about 60 nm and a +/−30 um field. Resolution should be between 30 nm and 40 nm. It will be understood that, aside from also passing through the SIL 572, Hydrogen Lyman-α light proceeds within the lens 550 in substantially the same manner as was discussed with respect to the lens 500 of FIG. 20A.

Embodiments of the present invention, including but not limited to the example optical microscopy, interferometric, and interferometric lithography systems disclosed above, can be employed in relation to a variety of different applications. For example, optical microscopes or interferometers in accordance with the present invention can be utilized in examining semiconductor wafers, biological (e.g., cellular/tissue) specimens, or optical recording surfaces, as well as in the research and development of MEMS (microelectromechanical systems), various metallurgical applications, the fabrication of various nanostructures for electronics and medical diagnostics, and writing via photomask lithography. Additionally, embodiments of the present invention also include other systems and methods that include one or more optical microscopy, interferometric, interferometric lithography, or other systems encompassed herein, or involve performing operations involving optical microscopy, interferometry, or interferometric lithography.

It should be appreciated that various embodiments of systems and methods encompassed herein are advantageous in various respects. For example, providing continuity to deep ultraviolet optical inspection is a desirable goal, and optical tools (which are different from EUV and e-beam based alternatives) have high throughput. With a shorter optical wavelength such as that of the Hydrogen Lyman-α line, checking for defects takes less time, and there is sufficient resolution to check areas of high spatial content and pinpoint defects. Another advantage of working in this regime is the availability of materials with reasonable transparency and also the capability of providing a numerical aperture (NA) advantage, as n sin(α/2). Higher throughput, shorter wavelength, and higher NA constitute a very attractive combination of advantages for photomask inspection in particular. In addition, the advantage of operating the mask sample in a non-vacuum environment, as can be achieved using Hydrogen Lyman-α light, eases handling requirements, equipment and operating costs. Combination of an interferometer utilizing Hydrogen Lyman-α light with a microscope for an ultra-high resolution surface profilometer can be particularly advantageous for application in the semiconductor industry.

Further for example, in biological studies, a vacuum ultraviolet (VUV) microscope can study unstained, living cells as nucleoproteins strongly absorb UV radiation. In fact, nucleic acids and nucleoproteins can be located as these regions appear darker than the rest of the cell, and the amount of nucleoproteins can be quantitatively determined. Recent interest in the interaction of VUV light with amino acids in the solid state can benefit through the use of a microscope employing Hydrogen Lyman-α light such as the microscopes discussed above. In some such embodiments, this type of measurement will employ a transmission configuration, which is a straightforward modification of an epi-illumination system. The prospect of significantly extending the range of excitable fluorophores and auto fluorescence with 10 eV photons is also potentially interesting for biology. Indeed, with the combined implementation of systems utilizing Hydrogen Lyman-α light such as those discussed above, along with new fluorescent compounds, techniques like Stimulated Emission Depletion (STED) can potentially push the sub-nanometer barrier, particularly where these studies are performed on or near surfaces (since the attenuation of Hydrogen Lyman-α light in water limits penetration to around 150 nm).

Although various embodiments which incorporate the teachings of the present invention have been shown and described in detail herein, those skilled in the art can readily devise many other varied embodiments that still incorporate these teachings. That is, it is specifically intended that the present invention not be limited to the embodiments and illustrations contained herein, but include modified forms of those embodiments including portions of the embodiments and combinations of elements of different embodiments as come within the scope of the following claims.

We claim:

1. An optical system comprising:
   at least one light source including a deep ultraviolet light source configured to generate first light having a wavelength within a window in the deep ultraviolet region of the electromagnetic spectrum within which a local minimum in the absorption coefficient of oxygen occurs that at standard temperature and pressure is less than 25 atm$^{-1}$ cm$^{-1}$, wherein the wavelength is approximately 121.6 nm, and wherein the at least one light source is further configured to generate second light that includes visible light or near-ultraviolet light and that is directed toward a target location to allow for locating of a feature of interest at the target location;

a lens device that receives at least a first portion of the generated first light, directs at least some of the first portion of the generated first light toward the target location, receives reflected light from the target location, and directs at least some of the reflected light toward a further location, wherein a region within a housing of the deep ultraviolet light source experiences a sub-atmospheric pressure and is substantially sealed off from an outside atmosphere, and wherein at least a part of a light path between the deep ultraviolet light source and the target location is other than at a high vacuum;

a camera device that is positioned at one of the further location and an additional location, wherein the camera device receives at least a second portion of the reflected light; and a beam splitter positioned between at least two of the deep ultraviolet light source, the lens device and the camera device, whereby an image is generated by the camera device based upon the second portion of the reflected light, wherein the optical system is an interferometer.

2. The optical system of claim 1, further comprising a mirror, wherein the beam splitter is positioned between the deep ultraviolet light source and the lens device, and wherein the beam splitter is also positioned between the mirror and the camera device.

3. The optical system of claim 2, wherein the camera device includes a light converter and the lens device includes an aspheric corrector, and wherein a difference between a first distance between the beam splitter and the mirror and a second distance between the beam splitter and the target location is less than a coherence length of the interferometer.

4. The optical system of claim 1, wherein the lens device includes a primary concave mirror, a secondary convex mirror, a field corrector, and a front diverger, and wherein the reflected light is received at the lens device by way of the field corrector, then is first received at the primary concave mirror, then is received at the secondary convex mirror, then passes through the front diverger, and subsequently proceeds to the further location.

5. The optical system of claim 4, wherein an additional solid immersion lens (SIL) is positioned between the field corrector and the target location.

6. An interferometric system comprising:
at least one light source including a deep ultraviolet light source configured to generate first light having a wavelength within a window in the deep ultraviolet region of the electromagnetic spectrum within which a local minimum in the absorption coefficient of oxygen occurs, wherein the wavelength is approximately 121.6 nm, and wherein the at least one light source is further configured to generate additional light that includes visible light or near-ultraviolet light and that is directed toward a target location to allow for locating of a feature of interest at the target location;

a lens device that receives a first portion of the generated first light and directs the first portion of the generated first light toward the target location, wherein a first region within a housing of the deep ultraviolet light source is substantially sealed off from an outside atmosphere, wherein at least a part of a first light path between the deep ultraviolet light source and the target location is other than at a high vacuum, and wherein the first light path extends through a location at which there is a sub-atmospheric pressure or an inert gas is present; and a beam splitting device that is positioned between the deep ultraviolet light source and the lens device, wherein interference occurs between a second portion of the generated first light and either the first portion of the generated first light or reflected light received by lens device from the target location after the first portion of the generated first light is directed toward the target location.

7. The interferometric system of claim 6, wherein the interferometric system includes an interferometer, wherein the beam splitting device includes a beam splitter, wherein the lens device receives the reflected light from the target location, and directs at least some of the reflected light toward a further location at which is positioned the beam splitter.

8. The interferometric system of claim 7, further comprising:
a camera system that is positioned at an additional location, wherein the camera system receives the reflected light and additionally receives the second portion of the generated first light, and wherein the camera system generates an image indicative of the interference between the second portion of the generated first light and the reflected light.

9. The interferometer of claim 8, further comprising a mirror, wherein the beam splitter is also positioned between the mirror and the camera device, wherein the first light path includes a first light path portion extending between the beam splitter and the target location, and wherein a second light path portion extends between the beam splitter and the mirror.

10. The interferometer of claim 9, wherein at least one of the housing or an additional housing forms a sealed enclosure within which is positioned the beam splitter, wherein the second light path portion extends only within the at least one housing, wherein a first subportion of the first light path portion extends only within the at least one housing, and wherein a second subportion of the first light path portion extends within an additional region outside of the at least one housing.

11. The interferometer of claim 10, wherein the sealed enclosure has Nitrogen gas therewithin, and wherein air at atmospheric pressure is in the additional region outside of the at least one housing, and wherein a difference in length between the first and second light path portions is less than a coherence length of the interferometer.

12. The interferometer of claim 7, wherein the lens device includes each of a phase plate and at least one refractive lens, wherein the phase plate includes an aspheric corrector, wherein the at least one refractive lens includes a first refractive lens and a second refractive lens, wherein the first refractive lens is positioned between the aspheric corrector and the second refractive lens, wherein the aspheric corrector is positioned in between the deep ultraviolet light source and the first refractive lens, and wherein the second refractive lens is positioned between the first refractive lens and the target location.

13. The interferometer of claim 12, wherein the lens device, a beam splitter, a mirror, an additional first lens positioned between the beam splitter and the deep ultraviolet light source, and an additional second lens positioned between the beam splitter and the camera device are positioned within at least one of the housing and an additional housing,
wherein the at least one housing also includes a window structure positioned between the second refractive lens of the lens device and the target location, and wherein the window structure permits the first portion of the generated first light to pass out of the housing but restricts air from entering the housing.

14. The interferometric system of claim 6, wherein the interferometric system includes an interferometric lithography system, and wherein the lens device includes a solid immersion lens (SIL) that directs both the receives the reflected light from the target location, and directs both the second portion of the generated first light and the first portion of the generated first light toward the target location.

15. The interferometric system of claim 14, wherein the beam splitting device includes either a reflective mask or a transmissive mask, and wherein the interferometric lithography system includes a plurality of mirrors for directing the second portion of the generated first light and the first portion of the generated first light toward the SIL.

16. An interferometric system comprising:
at least one light source including a deep ultraviolet light source configured to generate first light having a wavelength within a window in the deep ultraviolet region of the electromagnetic spectrum within which a local minimum in the absorption coefficient of oxygen occurs, wherein the wavelength is approximately 121.6 nm, and wherein the at least one light source is further configured to generate additional light that includes visible light or near-ultraviolet light and that is directed toward a target location to allow for locating of a feature of interest at the target location;
a lens device; and
a beam splitting device that is positioned between the deep ultraviolet light source and the lens device, wherein the beam splitting device is configured to direct a first portion of the generated first light toward a reference mirror by way of a reference path and to direct a second portion of the generated first light toward a target location by way of a test path,
wherein the deep ultraviolet light source and at least first parts of the reference path and test path are within a housing that is substantially sealed off from an outside atmosphere, wherein a second part of the test path extends through a first region at which there is a sub-atmospheric pressure or an inert gas is present so as to achieve negligible absorption of the generated first light, and wherein at least a third part of the test path between the deep ultraviolet light source and the target location is other than at a high vacuum or passes through a further region at which there is an ambient atmosphere; and
wherein the system is configured so that the beam splitting device receives both a first reflected amount of the first portion of the generated first light that was directed by way of the reference path and that was reflected at the reference mirror and also a second reflected amount of the second portion of the generated first light that was directed by way of the test path and that was reflected at the target location, and to experience interference between the first and second reflected amounts of the generated first light.

17. The interferometric system of claim 16, wherein the interferometric system includes an interferometer, wherein the beam splitting device includes a beam splitter, and wherein the lens device transmits the second reflected amount of the second portion of the generated first light toward the beam splitter.

18. The interferometric system of claim 17, further comprising:
a camera system that is positioned at an additional location, wherein the camera system receives the first reflected amount of the first portion of the generated first light that was directed by way of the reference path and also the second reflected amount of the second portion of the generated first light that was directed by way of the test path, and wherein the camera system generates an image indicative of the interference between the first and second reflected amounts.

19. The interferometric system of claim 18, wherein a difference between a reference path length of the reference path and a test path length of the test path is substantially equal to or less than 3.7 millimeters.

* * * * *